(12) United States Patent
Carr et al.

(10) Patent No.: US 10,518,005 B2
(45) Date of Patent: Dec. 31, 2019

(54) FLUID MANAGEMENT SYSTEM WITH PASS-THROUGH FLUID VOLUME MEASUREMENT

(71) Applicant: Thermedx, LLC, Solon, OH (US)

(72) Inventors: Douglas L. Carr, Chardon, OH (US); Nilesh R. Patel, Solon, OH (US)

(73) Assignee: Thermedx, LLC, Solon, OH (US)

( * ) Notice: Subject to any disclaimer, the term of this patent is extended or adjusted under 35 U.S.C. 154(b) by 158 days.

(21) Appl. No.: 15/706,822

(22) Filed: Sep. 18, 2017

(65) Prior Publication Data

US 2018/0000998 A1    Jan. 4, 2018

Related U.S. Application Data

(62) Division of application No. 14/710,810, filed on May 13, 2015, now Pat. No. 9,770,541.

(60) Provisional application No. 61/993,340, filed on May 15, 2014.

(51) Int. Cl.
*A61M 1/00* (2006.01)

(52) U.S. Cl.
CPC .......... *A61M 1/0007* (2014.02); *A61M 1/006* (2014.02); *A61M 1/0066* (2013.01); *A61M 2202/0007* (2013.01); *A61M 2202/0014* (2013.01); *A61M 2205/3368* (2013.01); *A61M 2205/3372* (2013.01); *A61M 2205/3393* (2013.01); *A61M 2205/3396* (2013.01); *A61M 2205/36* (2013.01); *A61M 2205/7536* (2013.01)

(58) Field of Classification Search
CPC .. A61M 1/0007; A61M 1/006; A61M 1/0066; A61M 2202/0007; A61M 2202/0014; A61M 2205/3368; A61M 2205/3372; A61M 2205/3393; A61M 2205/3396; A61M 2205/36; A61M 2205/7536
See application file for complete search history.

(56) References Cited

U.S. PATENT DOCUMENTS

| 3,410,268 A | 11/1968 | Leucci |
| 3,475,590 A | 10/1969 | Pins ............................. 392/470 |
| 3,515,137 A | 6/1970 | Santomieri ............. 604/165.02 |

(Continued)

FOREIGN PATENT DOCUMENTS

| EP | 0 776 670 | 6/1997 | ............. A61M 1/00 |
| EP | 0 575 512 | 5/1998 | ............. A61M 5/44 |

(Continued)

OTHER PUBLICATIONS

International Search Report and Written Opinion for International Application No. PCT/US2010/026698, dated Jun. 29, 2010.

(Continued)

*Primary Examiner* — Quynh-Nhu H. Vu
(74) *Attorney, Agent, or Firm* — Kusner & Jaffe

(57) ABSTRACT

A fluid management system including a pass-through fluid volume measurement system to provide continuous measurement of fluid returned from a surgical site during transit to a waste collection system. The pass-through fluid volume measurement system eliminates the need to physically replace full fluid collection containers during the medical procedure with new, empty fluid collection containers.

20 Claims, 14 Drawing Sheets

(56) References Cited

U.S. PATENT DOCUMENTS

| | | | |
|---|---|---|---|
| 4,180,074 A | 12/1979 | Murry et al. | 128/276 |
| 4,278,078 A | 7/1981 | Smith | 128/66 |
| 4,388,922 A | 6/1983 | Telang | 4/319 |
| 4,464,563 A | 8/1984 | Jewett | 219/298 |
| 4,574,876 A | 3/1986 | Aid | 165/46 |
| 4,759,749 A | 7/1988 | Verkaart | 604/113 |
| 4,844,074 A | 7/1989 | Kurucz | 128/401 |
| 4,898,518 A | 2/1990 | Hubbard et al. | 417/360 |
| 4,911,691 A | 3/1990 | Aniuk et al. | 604/164 |
| 5,013,303 A | 5/1991 | Tamari et al. | 604/140 |
| 5,050,266 A | 9/1991 | Schneider | 15/421 |
| 5,106,373 A | 4/1992 | Augustine et al. | 604/113 |
| 5,125,069 A | 6/1992 | O'Boyle | 392/465 |
| 5,137,509 A | 8/1992 | Freitas | 604/26 |
| 5,178,606 A | 1/1993 | Ognier et al. | 604/31 |
| 5,195,958 A | 3/1993 | Phillips | 604/33 |
| 5,224,929 A | 7/1993 | Remiszewski | 604/30 |
| 5,228,646 A | 7/1993 | Raines | 251/95 |
| 5,245,693 A | 9/1993 | Ford et al. | 392/470 |
| 5,250,032 A | 10/1993 | Carter, Jr. et al. | 604/113 |
| 5,254,094 A | 10/1993 | Starkey et al. | 604/113 |
| 5,271,086 A | 12/1993 | Kamiyama et al. | 392/483 |
| 5,303,735 A | 4/1994 | Cerola et al. | 137/596.2 |
| D350,822 S | 9/1994 | Lanigan | D24/111 |
| 5,347,992 A | 9/1994 | Pearlman et al. | 128/4 |
| 5,368,569 A | 11/1994 | Sanese | 604/113 |
| 5,381,510 A | 1/1995 | Ford et al. | 392/470 |
| 5,382,805 A | 1/1995 | Fannon et al. | 250/504 |
| 5,388,612 A | 2/1995 | Cerola et al. | 137/596.2 |
| 5,391,145 A | 2/1995 | Dorsey, III | 604/33 |
| D357,312 S | 4/1995 | Riquier et al. | D24/111 |
| 5,420,962 A | 5/1995 | Bakke | 392/470 |
| 5,427,144 A | 6/1995 | Teets et al. | 137/614.2 |
| 5,447,494 A | 9/1995 | Dorsey, III | 604/43 |
| 5,449,145 A | 9/1995 | Wortrich | 251/322 |
| 5,460,490 A | 10/1995 | Carr et al. | 417/44.2 |
| 5,496,314 A | 3/1996 | Eggers | 606/41 |
| 5,503,626 A * | 4/1996 | Goldrath | A61M 1/0058 604/65 |
| 5,505,710 A | 4/1996 | Dorsey, III | 604/158 |
| 5,520,638 A | 5/1996 | O'Quinn et al. | 604/67 |
| 5,522,796 A | 6/1996 | Dorsey, III | 604/118 |
| 5,522,805 A | 6/1996 | Vancaillie et al. | 604/246 |
| 5,551,448 A | 9/1996 | Matula et al. | 128/987 |
| 5,559,924 A | 9/1996 | Kadotani et al. | 392/483 |
| 5,562,640 A | 10/1996 | McCabe et al. | 604/280 |
| 5,573,504 A | 11/1996 | Dorsey, III | 604/35 |
| 5,586,977 A | 12/1996 | Dorsey, III | 604/264 |
| 5,607,391 A | 3/1997 | Klinger et al. | 604/33 |
| 5,626,563 A | 5/1997 | Dodge et al. | 604/153 |
| 5,643,203 A | 7/1997 | Beiser et al. | 604/66 |
| 5,683,381 A | 11/1997 | Carr et al. | 606/27 |
| 5,690,614 A | 11/1997 | Carr et al. | 604/114 |
| 5,709,670 A | 1/1998 | Vancaillie et al. | 600/573 |
| 5,729,653 A | 3/1998 | Magliochetti et al. | 392/485 |
| 5,733,263 A | 3/1998 | Wheatman | 604/141 |
| 5,803,510 A | 8/1998 | Dorsey, III | 285/148.23 |
| D398,051 S | 9/1998 | Lanigan et al. | D24/108 |
| 5,800,383 A | 9/1998 | Chandler et al. | 604/35 |
| 5,807,313 A | 9/1998 | Delk et al. | 604/35 |
| 5,807,332 A | 9/1998 | Augustine et al. | 604/113 |
| 5,810,770 A | 9/1998 | Chin et al. | 604/65 |
| 5,814,009 A | 9/1998 | Wheatman | 604/21 |
| 5,830,180 A | 11/1998 | Chandler et al. | 604/65 |
| 5,836,909 A | 11/1998 | Cosmescu | 601/35 |
| 5,875,282 A | 2/1999 | Jordan et al. | 392/470 |
| 5,882,339 A | 3/1999 | Beiser et al. | 604/131 |
| D409,748 S | 5/1999 | Lanigan et al. | D24/127 |
| 5,914,047 A | 6/1999 | Griffiths | 210/739 |
| 5,956,130 A * | 9/1999 | Vancaillie | A61B 5/02042 356/39 |
| 5,989,423 A | 11/1999 | Kamen et al. | 210/258 |
| 5,993,410 A | 11/1999 | Vincent et al. | 604/27 |
| 6,024,720 A | 2/2000 | Chandler et al. | 604/35 |
| 6,047,108 A | 4/2000 | Sword et al. | 392/470 |
| 6,074,363 A | 6/2000 | Beran et al. | 604/113 |
| 6,106,494 A | 8/2000 | Saravia et al. | 604/35 |
| 6,139,528 A | 10/2000 | Kistner et al. | 604/114 |
| 6,139,571 A | 10/2000 | Fuller et al. | 607/105 |
| 6,142,974 A | 11/2000 | Kistner et al. | 604/113 |
| 6,146,359 A | 11/2000 | Carr et al. | 604/114 |
| 6,149,622 A | 11/2000 | Marie | 604/43 |
| 6,149,674 A | 11/2000 | Borders | 607/96 |
| 6,175,688 B1 | 1/2001 | Cassidy et al. | 392/470 |
| 6,176,847 B1 | 1/2001 | Humphreys, Jr. et al. | 604/246 |
| 6,213,970 B1 | 4/2001 | Nelson et al. | 604/35 |
| 6,234,205 B1 | 5/2001 | D'Amelio et al. | 137/625.17 |
| 6,236,809 B1 | 5/2001 | Cassidy et al. | 392/470 |
| 6,238,366 B1 | 5/2001 | Savage et al. | 604/28 |
| 6,246,831 B1 | 6/2001 | Seitz et al. | 392/486 |
| 6,257,265 B1 | 7/2001 | Brunner et al. | 137/1 |
| 6,259,074 B1 | 7/2001 | Brunner et al. | 219/497 |
| 6,261,261 B1 | 7/2001 | Gordon | 604/113 |
| 6,336,003 B1 | 1/2002 | Mitsunaga et al. | 392/470 |
| 6,358,224 B1 | 3/2002 | Tims et al. | 604/30 |
| 6,406,470 B1 | 6/2002 | Kierce | 604/535 |
| 6,413,233 B1 | 7/2002 | Sites et al. | 604/6.13 |
| 6,464,666 B1 | 10/2002 | Augustine et al. | 604/113 |
| 6,527,743 B1 | 3/2003 | Fowler et al. | 604/131 |
| 6,535,689 B2 | 3/2003 | Augustine et al. | 392/470 |
| 6,572,641 B2 | 6/2003 | Brugger et al. | 607/106 |
| 6,572,689 B2 | 6/2003 | Cosby, II et al. | 96/242 |
| 6,585,708 B1 | 7/2003 | Maaskamp | 604/317 |
| 6,595,957 B1 | 7/2003 | Griffiths et al. | 604/156 |
| 6,602,221 B1 | 8/2003 | Saravia et al. | 604/31 |
| 6,620,130 B1 | 9/2003 | Ginsburg | 604/113 |
| 6,635,031 B2 | 10/2003 | Fowler et al. | 604/131 |
| 6,635,034 B1 | 10/2003 | Cosmescu | 604/289 |
| 6,641,556 B1 | 11/2003 | Shigezawa | 604/113 |
| 6,645,232 B2 | 11/2003 | Carson | 607/104 |
| 6,648,906 B2 | 11/2003 | Lasheras et al. | 607/105 |
| 6,652,488 B1 | 11/2003 | Cover et al. | 604/118 |
| 6,685,667 B1 | 2/2004 | Delk et al. | 604/30 |
| 6,699,184 B2 | 3/2004 | Felix et al. | 600/156 |
| 6,699,267 B2 | 3/2004 | Voorhees et al. | 607/104 |
| 6,722,782 B2 | 4/2004 | Faries, Jr. et al. | 374/162 |
| 6,743,201 B1 | 6/2004 | Donig et al. | 604/114 |
| 6,775,473 B2 | 8/2004 | Augustine et al. | 392/470 |
| 6,788,885 B2 | 9/2004 | Mitsunaga et al. | 392/470 |
| 6,824,528 B1 | 11/2004 | Faries, Jr. et al. | 604/113 |
| 6,875,198 B2 | 4/2005 | Foley | 604/119 |
| 6,882,797 B2 | 4/2005 | Stewart et al. | 392/470 |
| 6,899,697 B2 | 5/2005 | Fowler et al. | 604/131 |
| 6,901,216 B2 | 5/2005 | Jusiak et al. | 392/470 |
| 6,918,902 B2 | 7/2005 | French et al. | 604/500 |
| 6,958,058 B1 | 10/2005 | Hunter, Sr. et al. | 604/500 |
| 6,997,942 B2 | 2/2006 | Machold et al. | 607/96 |
| 7,004,960 B2 | 2/2006 | Daoud | 607/105 |
| 7,010,221 B2 | 3/2006 | Augustine et al. | 392/470 |
| 7,031,602 B2 | 4/2006 | Faries, Jr. et al. | 392/470 |
| 7,083,601 B1 | 8/2006 | Cosmescu | 604/289 |
| 7,094,219 B2 | 8/2006 | Noice et al. | 604/113 |
| 7,153,285 B2 | 12/2006 | Lauman et al. | 604/6.08 |
| 7,158,719 B2 | 1/2007 | Cassidy | 392/494 |
| 7,164,852 B2 | 1/2007 | Cazzini et al. | 392/470 |
| 7,204,821 B1 * | 4/2007 | Clare | A61M 1/0031 137/102 |
| 7,207,966 B2 | 4/2007 | Savare et al. | 604/27 |
| 7,232,457 B2 | 6/2007 | Schmidt et al. | 607/96 |
| 7,236,694 B1 | 6/2007 | Chammas | 392/470 |
| 7,238,170 B2 | 7/2007 | Park | 604/113 |
| 7,258,711 B2 | 8/2007 | Dunn et al. | 55/385.1 |
| 7,261,557 B2 | 8/2007 | Gill et al. | 431/328 |
| 7,273,359 B2 | 9/2007 | Blight et al. | 417/477.13 |
| 7,297,133 B2 | 11/2007 | Nelson et al. | 604/35 |
| 7,316,666 B1 | 1/2008 | Entenman et al. | 604/113 |
| 7,394,976 B2 | 7/2008 | Entenman et al. | 392/470 |
| 7,410,475 B2 | 8/2008 | Krensky et al. | 604/29 |
| 7,458,951 B2 | 12/2008 | Lauman et al. | 604/6.08 |
| 7,621,898 B2 | 11/2009 | Lalomia et al. | 604/319 |
| D615,191 S | 5/2010 | McGill et al. | D24/111 |
| D616,539 S | 5/2010 | McGill | D24/111 |
| 7,753,880 B2 | 7/2010 | Malackowski | 604/131 |
| 7,762,989 B2 | 7/2010 | Simpson | 604/151 |

(56) References Cited

U.S. PATENT DOCUMENTS

| | | | |
|---|---|---|---|
| D650,896 S | 12/2011 | McGill et al. | D24/111 |
| 8,123,731 B2 | 2/2012 | Ryan | 604/317 |
| 8,138,925 B2 | 3/2012 | Downie et al. | 340/572.8 |
| 8,388,570 B2 | 3/2013 | Kumar et al. | 604/30 |
| 8,562,577 B2 | 10/2013 | Michaels et al. | 604/317 |
| 8,652,089 B2 | 2/2014 | Kumar et al. | 604/30 |
| 9,492,071 B2 | 11/2016 | Woolford et al. | A61B 1/317 |
| 2002/0032403 A1 | 3/2002 | Savagle et al. | 604/28 |
| 2002/0096984 A1 | 7/2002 | Konishi et al. | 313/25 |
| 2003/0004470 A1 | 1/2003 | Hickerson et al. | 604/251 |
| 2003/0109826 A1 | 6/2003 | Fowler et al. | 604/131 |
| 2003/0135250 A1 | 7/2003 | Lauman et al. | |
| 2003/0176833 A1 | 9/2003 | Libermann | 604/65 |
| 2003/0212363 A1 | 11/2003 | Shipp | 604/118 |
| 2003/0216689 A1 | 11/2003 | Bouhuijs et al. | 604/113 |
| 2004/0097872 A1 | 5/2004 | Delk et al. | 604/67 |
| 2004/0190884 A1 | 9/2004 | Stewart et al. | 392/470 |
| 2004/0204679 A1 | 10/2004 | Visconti et al. | 604/131 |
| 2005/0055074 A1 | 3/2005 | Tak et al. | 607/104 |
| 2005/0095155 A1 | 5/2005 | Blight et al. | 417/477.13 |
| 2005/0142013 A1 | 6/2005 | Faries, Jr. et al. | 414/477.2 |
| 2005/0148934 A1 | 7/2005 | Martens et al. | 604/113 |
| 2006/0122576 A1 | 6/2006 | Raja et al. | 604/890.1 |
| 2006/0148279 A1 | 7/2006 | German et al. | 439/49 |
| 2006/0210255 A1 | 9/2006 | Cassidy | 392/470 |
| 2006/0222350 A1 | 10/2006 | Cassidy | 392/470 |
| 2006/0253075 A1 | 11/2006 | Faries, Jr. et al. | 604/113 |
| 2007/0045272 A1 | 3/2007 | French et al. | 219/216 |
| 2007/0129707 A1 | 6/2007 | Blott et al. | 604/543 |
| 2007/0142773 A1 | 6/2007 | Rosiello et al. | 604/113 |
| 2007/0142775 A1 | 6/2007 | Visconti et al. | 604/131 |
| 2007/0159337 A1 | 7/2007 | Tethrake et al. | 340/572.8 |
| 2007/0161978 A1 | 7/2007 | Fedenia et al. | 604/34 |
| 2007/0217948 A1 | 9/2007 | Ghelli et al. | 422/45 |
| 2007/0233003 A1 | 10/2007 | Radgowski et al. | 604/151 |
| 2007/0242934 A1 | 10/2007 | Entenman et al. | 392/465 |
| 2007/0265689 A1 | 11/2007 | Frey | 607/105 |
| 2007/0278155 A1 | 12/2007 | Lo et al. | |
| 2008/0021377 A1 | 1/2008 | Kienman et al. | |
| 2008/0031773 A1 | 2/2008 | Eccleston | 422/44 |
| 2008/0039815 A1 | 2/2008 | Ogawa | 604/408 |
| 2008/0077087 A1 | 3/2008 | Martens | 604/113 |
| 2008/0093276 A1 | 4/2008 | Roger et al. | 210/104 |
| 2008/0145249 A1 | 6/2008 | Smisson et al. | 417/474 |
| 2008/0154095 A1 | 6/2008 | Stubkjaer et al. | 600/156 |
| 2008/0200866 A1 | 8/2008 | Prisco et al. | |
| 2009/0008306 A1 | 1/2009 | Cicchello et al. | 210/85 |
| 2009/0009290 A1 | 1/2009 | Kneip et al. | 340/10 |
| 2010/0151785 A1 | 6/2010 | Steeger et al. | 455/41.1 |
| 2010/0152656 A1 | 6/2010 | Music | 604/119 |
| 2010/0228222 A1 | 9/2010 | Williams et al. | 604/500 |
| 2010/0228224 A1* | 9/2010 | Pyles | A61M 1/0058 604/500 |
| 2011/0144812 A1 | 6/2011 | Davis et al. | 700/281 |
| 2011/0162333 A1 | 7/2011 | Cook et al. | 53/507 |
| 2011/0288524 A1 | 11/2011 | Gelfand et al. | 604/503 |
| 2012/0022441 A1 | 1/2012 | Kelly et al. | 604/29 |
| 2012/0271110 A1* | 10/2012 | Kumar | A61B 1/00068 600/156 |
| 2013/0079702 A1 | 3/2013 | Klein et al. | 604/22 |
| 2013/0345621 A1 | 12/2013 | Cicchello et al. | 604/22 |
| 2014/0217029 A1 | 8/2014 | Meyer et al. | 210/647 |
| 2015/0119795 A1* | 4/2015 | Germain | A61M 3/0229 604/28 |
| 2016/0151557 A1 | 6/2016 | Woolford et al. | 606/86 R |

FOREIGN PATENT DOCUMENTS

| | | | |
|---|---|---|---|
| EP | 1100574 A1 | 5/2001 | |
| GB | 2 242 367 | 10/1991 | A61M 1/32 |
| WO | WO 87/00759 | 2/1987 | A61M 7/00 |
| WO | WO 1992/017040 | 10/1992 | H05B 1/02 |
| WO | WO 96/13216 | 5/1996 | A61B 17/36 |
| WO | WO 2000/047283 | 8/2000 | A61N 5/04 |
| WO | WO 2004/018295 A2 | 3/2004 | |
| WO | WO 2009/036818 A1 | 3/2009 | |
| WO | WO 2010/104878 | 9/2010 | A61M 1/00 |

OTHER PUBLICATIONS

The Surgical Company, Fluido® Product Information obtained from website www.fluido.nl, Jan. 18, 2008.

Smiths-Medical.com, Blood & Fluid Warming Systems (Level 1®) H-1200 Fast Flow Fluid Warmer with Integrated Air Detector/Clamp, 2008.

Ranger Blood/Fluid Warming, Ranger® Blood and Fluid Warming Systems Product Specifications, 2008.

Paladin Biomedical Corporation, In-Line Microwave Fluid Warming Technology, T900™ system, 2004.

Smiths-Medical.com, Blood & Fluid Warming Systems (Level 1®), NormoFlo® Irrigating System, Level 1, 2008.

Ranger Irrigation Fluid Warming, Ranger® Blood and Fluid Warming Systems, Ranger Irrigation Fluid Warming System, 2008.

Socomed, Endoflow® by Socomed, slide presentation, prior to Sep. 2008.

Stryker® UK, Strykflow 2 Suction & Irrigation System, 2008.

Stryker, Stryket AHTO™ Irrigation System, Dec. 2004.

Olympus, Surgiflow, Irrigation Pump, Feb. 2006.

Olympus, Surgipump, Suction/Irrigation Pump, Feb. 2006.

Olympus, Eco-Pump, Irrigation Pump, Feb. 2006.

CardinalHealth, Hydroline® and PulseWave® Laparoscopic Suction/Irrigation Systems, 2003.

Gaymar®, Medi-Temp III™, Blood/Fluid Warming, prior to Sep. 2008.

Belmont Instrument Corporation, FMS 2000 Rapid Infuser, 2003.

Belmont Instrument Corporation, buddy™, Fluid Warmer, 2003.

Astotherm®, Astotherm® plus 220, Blood and Infusion Warmer, prior to Sep. 2008.

Futuremed®, Animec™ AM-2S, Fluid Warmer, 2000-2007.

Vital Signs Inc., Medical Products, enFlow®, IV Fluid/Blood Warming System, prior to Sep. 2008.

Smiths-Medical.com, Blood & Fluid Warming Systems (Level 1®) HOTLINE® Blood and Fluid Warmer, 2008.

Stryker®, Pulsed Lavage, Interpulse—Pulsed Lavage, Wound Care, 2008.

Simpulse* VariCare* System, Wound Management, 2007.

Zimmer, Pulsavac®, Wound Debridement System, 1998.

Zimmer, Pulsavac Plus System, Wound Debridement System, Nov. 2, 2005.

Zimmer, Pulsavac Plus AC, Wound Debridement System, Jun. 8, 2008.

Richard Wolf Medical Instruments Corporation, The Richard Wolf Fluid Manager, Hysteroscopic Fluid Monitoring, prior to Sep. 2008.

Olympus, Fluid Management Products, Dolphin® II and Disten-U-Flo Fluid Management Systems for Hysteroscopy, 2008.

Olympus, HysteroFlow/HysteroBalance, Fluid Management, prior to Sep. 2008.

Stryker, Stryker Fluid Management, FluidSafe Fluid Management System, prior to Sep. 2008.

Young, RN. et al., Perioperative Fluid Management, AORN Journal, vol. 89, No. 1, Jan. 2009, pp. 167-183.

Smith et al., Principles of Fluid and Blood Warming in Trauma, International TraumaCare (ITACCS), vol. 18, No. 1, 2008, pp. 71-79.

Bard, Medical Division, Company Information obtained from website www.bardmedical.com, Jan. 29, 2008.

C Change Surgical, Press Release obtained from website www.cchangesurgical.com, Jul. 24, 2007.

C Change Surgical, IntraTemp™, Product Information obtained from website www.cchangesurgical.com, Jan. 18, 2008.

C Change Surgical, Press Releases, Jul. 2004-Feb. 2008.

CardinalHealth, Medi-Vac® Suction and Wound and Drainage Product Information obtained from website www.cardinal.com, Jan. 18, 2008.

Davol Inc., Laparoscopy Surgical Product Information obtained from website www.davol.com, Jan. 18, 2008.

(56) References Cited

OTHER PUBLICATIONS

Ethicon, Inc., Product Catalog obtained from website ecatalog.ethicon.com, Jan. 18, 2008.
Johnson & Johnson Gateway®, Product Information, Fluid Management System, obtained from website www.jnjgateway.com, Jan. 18, 2008.
Gyrus ACMI, Gyrus Medical, Niagara TRS® Thermal Retention System Product Information obtained from website www.acmicorp.com, Jan. 18, 2008.
Innercool Therapies, Inc., Celsius Control System™, Product Information obtained from website www.innercool.com, Jan. 28, 2008.
Medical Solutions, Inc., Fluid Warming System, Product Information obtained from website www.warmiv.com, Jan. 25, 2008.
Nellcor Press Release, Nellcor Expands Warmflo Fluid and Blood Warming Solutions with New Warming Cassette, obtained from website www.cyperus.com, Jan. 18, 2008.
Nellcor, Products Listing obtained from website www.nellcor.com, Jan. 18, 2008.
Nellcor, Warmflo® Pressure Infusor Product Information obtained from website www.nellcor.com, Oct. 2, 2007.
Nellcor, Warmflo® Fluid Warming System Brochure, 2002.
Olympus, High Definition Video Laparoscopes, HD Endoeye™, Product Information obtained from website www.olympussurgical.com, Jan. 24, 2008.
Olympus, UHI-3 High Flow Insufflation Unit Product Information obtained from website www.olympusmedical.co.kr, Jan. 18, 2008.
Olympus, UHI-3 High Flow Insufflation Unit Product Information obtained from website www.olympusaustralia.com.au, Jan. 18, 2008.
Paladin Biomedical Corporation, ThermoStat™ 900 Blood and Fluid Warmer Product Information obtained from paladinbiomedical.com, Jan. 22, 2008.
Radiant Medical, Inc. Company Profile obtained from Silicon Valley/San Jose Business Journal website www.bizjournals.com, Jan. 25, 2008.
Radiant Medical, Inc. Press Release, Oct. 12, 2005.
Sanese Medical Corp., Thermo-Flo System 3, Product Information, search results for "new products" search of website speechtherapist.com, pp. 4-5, Jan. 18, 2008.
Karl Storz, Suction and Irrigation Systems Product Information obtained from website www.websurg.com, Jan. 28, 2009.
Stryker, Endoscopy, Stryket AHTO™ Irrigation System Product Catalog, Dec. 2004.
Stryker® Instruments, Orthopedics, InterPulse Battery Powered Irrigation Product Catalog, prior to Sep. 2008.
Stryker, Stryker StrykeFlow 2 Product Information obtained from website www.stryker.com, Jan. 18, 2008.
Stryker, Stryker AHTO Irrigation System Product Information obtained from website www.stryker.com, Jan. 18, 2008.
TSCI Company Profile obtained from website www.fluido.nl, Jan. 18, 2008.
TSCI Press Release obtained from website www.fluido.nl, Jan. 18, 2008.
CystoMedix, Company/Product Information obtained from website www.cystomedix.com, Jan. 28, 2010.

\* cited by examiner

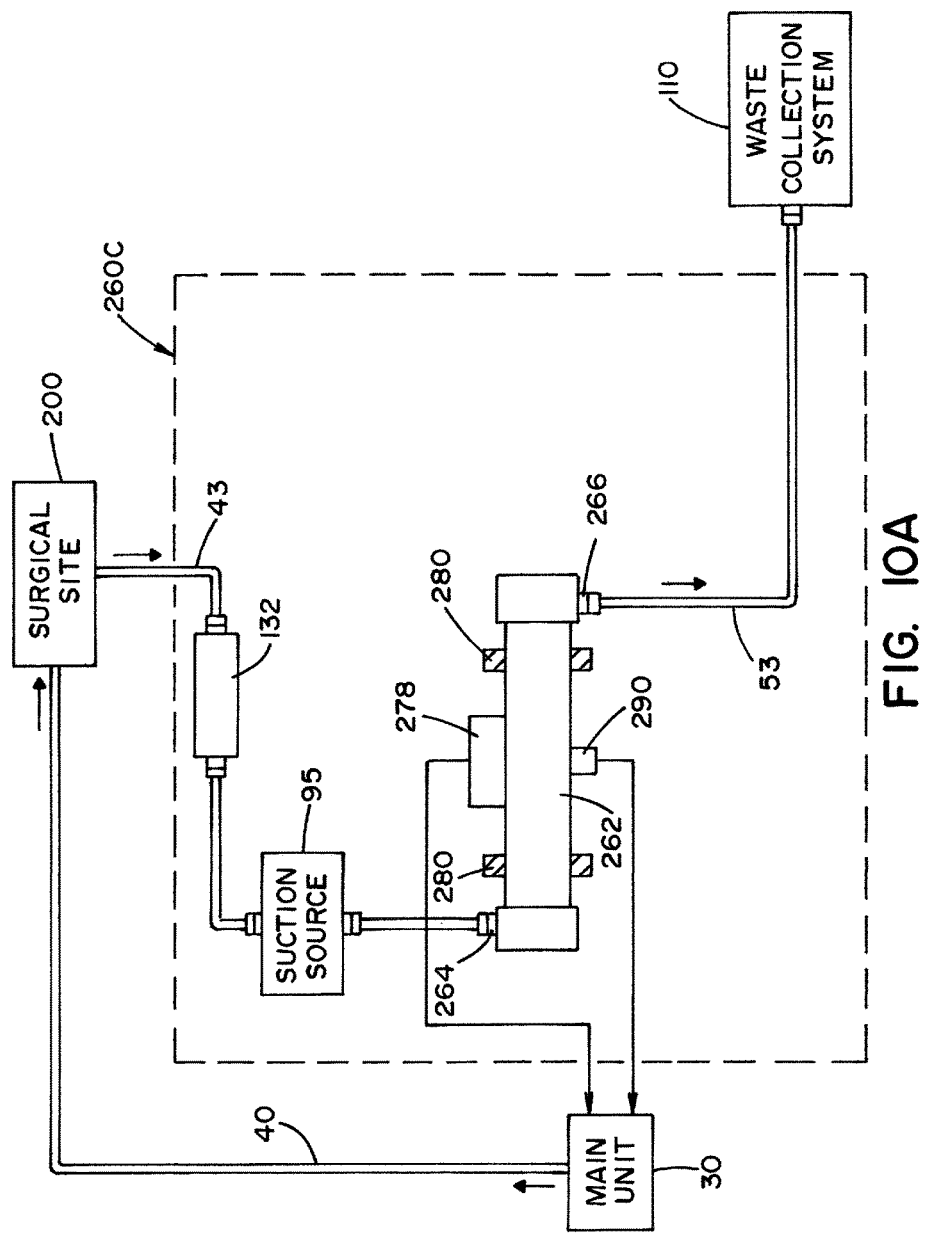

FLUID MANAGEMENT SYSTEM WITH PASS-THROUGH FLUID VOLUME MEASUREMENT

RELATED APPLICATIONS

This application is a divisional of U.S. application Ser. No. 14/710,810, filed May 13, 2015 (now U.S. Pat. No. 9,770,541, issued Sep. 26, 2017), which claims the benefit of U.S. Provisional Application No. 61/993,340, filed May 15, 2014, said patent applications herein fully incorporated by reference.

FIELD OF THE INVENTION

The present invention relates generally to fluid management systems used during surgical procedures to provide one or more functions associated with irrigation, distention, fluid warming, fluid deficit monitoring, suction, and the like, and more particularly relates to a method and apparatus for continuously measuring the volume of fluid being returned from the surgical site as it is being delivered to a waste collection system.

BACKGROUND OF THE INVENTION

A fluid management system (FMS) may be used in connection with a wide variety of medical procedures involving one or more fluid delivery functions including, but not limited to: fluid irrigation; distention of a body cavity; fluid warming; fluid deficit monitoring associated with delivery and return of fluid to/from a surgical site; and suction. The medical procedures may be associated with multiple surgical disciplines including, but not limited to: gynecologic, urologic, orthopedic, colorectal, and general surgical procedures.

During certain medical procedures, patient safety may require that the amount of fluid delivered to the surgical site and the amount of fluid returned from the surgical site be continuously monitored to determine the "fluid deficit." Accordingly, a FMS may be configured to provide a fluid deficit monitoring function to accurately measure fluid inflow (to the surgical site) and outflow (from the surgical site), and to calculate a fluid deficit in order to monitor a patient's fluid absorption level during a medical procedure as excess fluid absorption can result in serious complications. Typically, fluid returning from the surgical site is collected in one or more fluid collection containers (e.g., canisters). The volume of fluid collected from the surgical site is typically determined by measuring weight. A fluid deficit is then calculated by comparing the volume of fluid delivered to the surgical site with the volume of fluid returned from the surgical site.

Canisters are frequently used as fluid collection containers. When a canister fills with fluid to a maximum capacity during a medical procedure, it becomes necessary to remove the full canister and replace it with a new, empty canister. There are several drawbacks to removing and replacing canisters during a medical procedure. In this regard, such activity can (i) disrupt the medical procedure by necessitating the suspension of suction used to remove fluid from the surgical site, and thereby cause a suspension of fluid deficit monitoring; (ii) cause inconvenience to medical personnel, especially in surgical procedures involving high fluid volumes, as medical personnel have to physically remove full canisters and replace them with new, empty canisters; (iii) potentially introduce errors into fluid deficit monitoring calculations due to disruption of the fluid management system during the canister replacement process (e.g., bumping or moving), which can adversely affect the ability of the fluid management system to accurately weigh the remaining and new canisters; (iv) potentially introduce errors into fluid deficit monitoring calculations due to leaks and spills caused by detaching tubing used to return fluid from the surgical site from full canisters and reattaching such lines to the new, empty canisters, and (v) increase the cost of a surgical procedure by requiring that a number of canisters be used during a surgical procedure which is commensurate with the amount of fluid used.

In view of the foregoing, there is a need for a fluid management system that incorporates a "pass-through" fluid volume measurement system that continuously measures the volume of fluid returning from a surgical site during transit to a waste collection system (e.g., a dedicated fluid collection system or a hospital's waste disposal system) and eliminates the need to replace full canisters with new, empty canisters during a medical procedure.

SUMMARY OF THE INVENTION

In accordance with the present invention, there is provided a fluid management system comprising: at least one fluid supply container for storing a fluid to be delivered to a surgical site; a pump for delivering the fluid from the at least one fluid supply container to the surgical site; and a pass-through fluid volume measurement system for determining the volume of fluid returned from the surgical site, said pass-through fluid volume measurement system comprising: a plurality of fluid collection containers, wherein each fluid collection container has (i) a suction input in fluid communication with a suction line for drawing a vacuum in the fluid collection container, (ii) a fluid input in fluid communication with a fluid return line for receiving fluid returning from the surgical site, and (iii) a fluid output in fluid communication with a fluid output line for evacuating the fluid collected in the fluid collection container to a waste collection system; one or more weight sensors for providing signals indicative of the sensed weight of the fluid collection containers; and a plurality of valves moveable between open and closed positions to control the flow of fluid through the suction line, the fluid return line and the fluid output line; a suction source for providing suction in the suction line to draw a vacuum in the fluid collection containers to thereby draw fluid from the surgical site into the fluid collection containers, and for providing suction in the fluid output line to draw fluid collected in the fluid collection containers into the waste collection system; and a control unit for receiving the signals from the one or more weight sensors to monitor a volume of fluid returned from the surgical site to the fluid collection containers, and moving the plurality of valves between the open and the closed positions to alternately fill one of the fluid collection containers while emptying another of the fluid collection containers.

In accordance with another aspect of the present invention, there is provided a fluid management system comprising: at least one fluid supply container for storing a fluid to be delivered to a surgical site; a pump for delivering the fluid from the at least one fluid supply container to the surgical site; and a pass-through fluid volume measurement system for determining the volume of fluid returned from the surgical site, said pass-through fluid volume measurement system comprising: a support member for supporting components of the pass-through fluid volume measurement system; a flow sensing device including: a disposable or single-use fluid measurement tube having an inlet port in fluid communication with a fluid return line for receiving fluid returning from the surgical site, and an outlet port in fluid communication with a fluid output line for receiving the fluid exiting the fluid measurement tube, at least one ultrasonic sensor for providing a signal indicative of the flow rate of fluid passing through the fluid measurement tube, and a clamping mechanism mounted to the support member, said clamping mechanism for temporarily mounting the fluid measurement tube in a proper orientation between the inlet and outlet ultrasonic sensors; a suction source for providing suction in the fluid return line and fluid output line to draw the fluid through the fluid measurement tube and subsequently into a waste collection system; and a control unit for receiving the signals from the inlet and outlet sensors to monitor a volume of fluid returned from the surgical site.

In accordance with still another aspect of the present invention, there is provided a method for continuously measuring a volume of fluid being returned from a surgical site as it is being delivered to a waste collection system, said method comprising: filling the first fluid collection container, by: opening a valve associated with a suction line in fluid communication with a first fluid collection container; opening a valve associated with a fluid return line in fluid communication with the first fluid collection container; closing a valve associated with a fluid output line in fluid communication with the first fluid collection container; closing a valve associated with a suction line in fluid communication with a second fluid collection container; and closing a valve associated with a fluid return line in fluid communication with the second fluid collection container; upon filling the first fluid collection container with fluid to a predetermined volume, emptying the first fluid collection container and filling the second fluid collection container, by closing the valve associated with a suction line in fluid communication with a first fluid collection container; closing the valve associated with a fluid return line in fluid communication with the first fluid collection container; opening the valve associated with a fluid output line in fluid communication with the first fluid collection container; opening the valve associated with a suction line in fluid communication with a second fluid collection container; opening the valve associated with a fluid return line in fluid communication with the second fluid collection container; and closing a valve associated with a fluid output line in fluid communication with the second fluid collection container; and alternately filling and emptying the first and second fluid collection containers until a medical procedure is completed.

In accordance with yet another aspect of the present invention, there is provided a method for continuously measuring a volume of fluid being returned from a surgical site as it is being delivered to a waste collection system, said method comprising the steps of: drawing fluid from the surgical site through a flow sensing device providing signals indicative of a fluid flow rate; monitoring the volume of fluid passing through the flow sensing device using the signals indicative of the fluid flow rate; and passing the fluid from the flow sensing device to the waste collection system until a medical procedure is completed.

An advantage of the present invention is the provision of a fluid management system that continuously measures the volume of fluid returning from a surgical site during transit to a waste collection system.

Another advantage of the present invention is the provision of a fluid management system that eliminates the need to replace full fluid collection containers with new, empty fluid collection containers during a medical procedure.

A still further advantage of the present invention is the provision of a fluid management system having a stand-alone pass-through fluid volume measurement system.

Yet another advantage of the present invention is the provision of a fluid management system capable of fluid delivery, suction, fluid removal/collection, fluid deficit monitoring, and fluid disposal.

These and other advantages will become apparent from the following description of illustrated embodiments taken together with the accompanying drawings and the appended claims

BRIEF DESCRIPTION OF THE DRAWINGS

The invention may take physical form in certain parts and arrangement of parts, embodiments of which will be described in detail in the specification and illustrated in the accompanying drawings which form a part hereof, and wherein:

FIG. 10A is a schematic diagram of the pass-through fluid volume measurement system shown in FIG. 10, as modified to include a single ultrasonic sensor for sensing fluid flow.

DETAILED DESCRIPTION OF THE INVENTION

Figure 1:
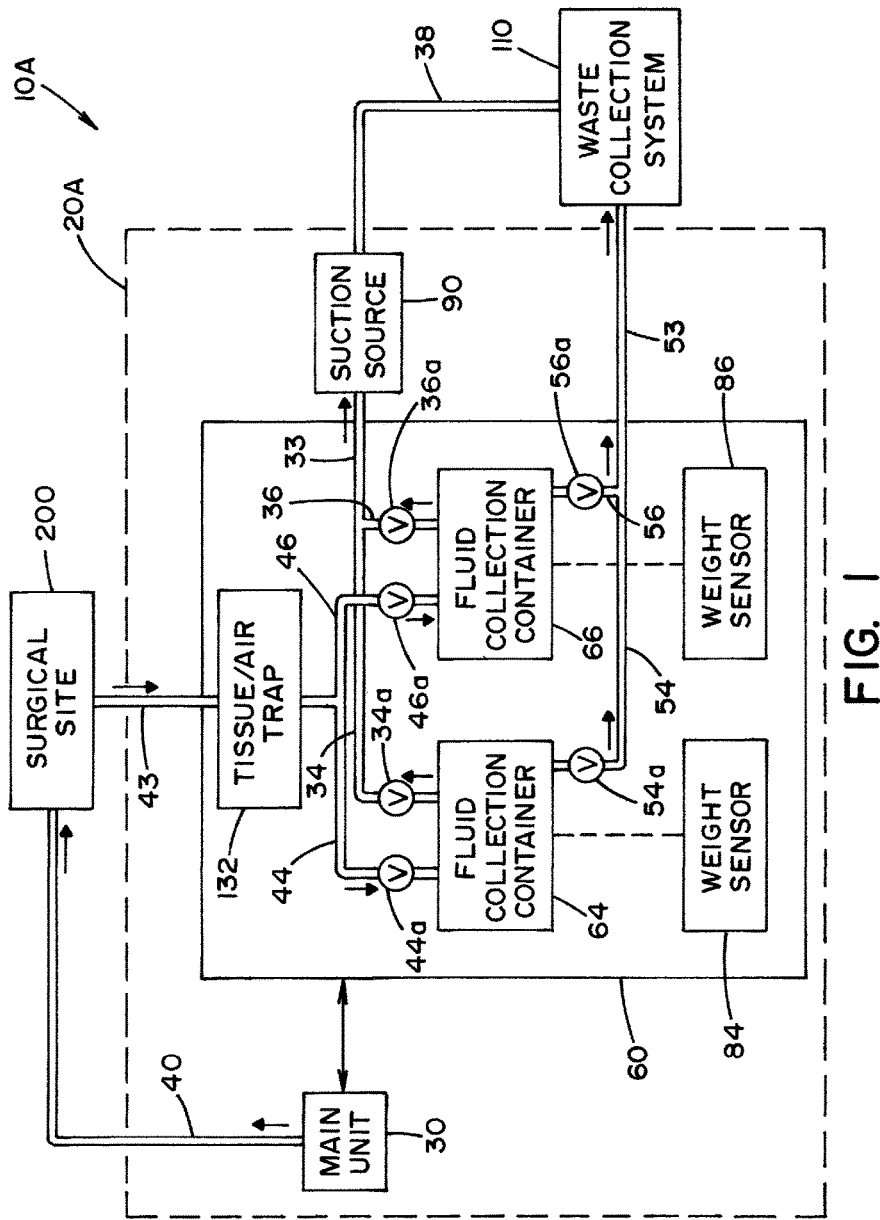
FIG. 1 is a schematic diagram illustrating an FMS according to a first embodiment of the present invention, wherein the FMS includes a fluid management unit having a pass-through fluid volume measurement system and an integrated suction source for return of fluid from the surgical site and subsequent evacuation of the fluid returned from the surgical site to a waste collection system.

Referring now to the drawings wherein the showings are for the purposes of illustrating embodiments of the invention only and not for the purposes of limiting same, FIG. 1 shows a fluid management system (FMS) 10A according to a first embodiment of the present invention. FMS 10A is a multi-functional system that supplies fluid to a surgical site 200, removes fluid from surgical site 200, monitors a fluid deficit, and disposes of fluid returned from surgical site 200, as will be described in detail below. It should be appreciated that the term "surgical site" as used herein refers not only to the patient's body where a surgery is being performed, but also to the general region surrounding the patient.

FMS 10A is generally comprised of a fluid management unit 20A including a main unit 30, a pass-through fluid volume measurement system 60 and an integrated suction source 90. Fluid management unit 20A interfaces with a waste collection system 110, as will be described below. It should be appreciated that suction source 90 may alternatively be arranged as a component of measurement system 60.

As seen in FIG. 1, a fluid supply line 40 provides a fluid conduit between main unit 30 and surgical site 200, a fluid return line 43 provides a fluid conduit between measurement system 60 and surgical site 200, a suction line 33 provides a fluid conduit between suction source 90 and measurement system 60, a suction line 38 provides a fluid conduit between suction source 90 and waste collection system 110, and a fluid output line 53 provides a fluid conduit between measurement system 60 and waste collection system 110. Supply line 40, return line 43, suction line 33, suction line 38, and output line 53 may take the form of fluid conduits, such as conventional medical grade flexible plastic tubing.

Main unit 30 includes a control unit comprised of components such as a microprocessor or microcontroller, memory device(s), data storage device(s), output device(s) (e.g., LCD screen, touch screen, conventional display device, audio speaker, printer, and the like), and input device(s) (e.g., touch screen, keypad, keyboard, mouse, mechanical switching devices, and the like). Main unit 30 may also include one or more fluid container supports (such as hangers or hooks) for supporting one or more fluid supply containers (e.g., fluid bags) that store fluid that is to be delivered to a surgical site 200, weight sensors for detecting the weight of fluid in the fluid supply containers, and a pump for pressurizing fluid in the fluid supply containers and delivering the fluid to surgical site 200 via fluid supply line 40. For example, fluid supply line may be connected with a surgical instrument to facilitate a surgical procedure. It should be appreciated that gravity or other means of fluid pressurization may be substituted for the pump. Main unit 30 may also include numerous other components for regulating fluid flow, fluid pressure, fluid temperature (e.g., a fluid heating apparatus), and the like. The control unit controls the supply of fluid delivered to surgical site 200 via fluid supply line 40, monitors the volume of fluid supplied to surgical site 200 (via supply line 40), monitors the volume of fluid returned from surgical site 200 (via return line 43), and determines a fluid deficit. A detailed description of the components and operation of an exemplary fluid management unit, including fluid deficit monitoring, is provided in U.S. Pat. No. 8,444,592, issued May 21, 2013, which is fully incorporated herein by reference.

Pass-through fluid volume measurement system 60 determines the volume of fluid removed from surgical site 200 via fluid return line 43. According to the illustrated embodiment, measurement system 60 includes a first fluid collection container 64, a second fluid collection container 66, and first and second weight sensors 84, 86 respectively associated with fluid collection containers 64, 66. It is contemplated that fluid collection containers 64, 66 may take a variety of forms, including, but not limited to, disposable or re-usable rigid hard-shell canisters, rigid hard-shell canisters with disposable or reusable liners, disposable pouches or bags having a rigid skeleton, fluid containers supportable from mounting brackets or hooks.

The end of return line 43 located at surgical site 200 may include a plurality of input lines that are combined by a manifold. Each of these input lines may be located at different locations at surgical site 200. For example, the input lines may collect fluid from the patient, floor suctioning equipment, a fluid collection drape, and surgical instrument outflow ports.

In the embodiment shown in FIG. 1, the end of return line 43 fluidly connected with measurement system 60 includes a first branch 44 and a second branch 46 for fluid communication with fluid inputs (e.g., input tubes) of fluid collection containers 64 and 66, respectively. Branches 44 and 46 may be joined by a y-connector. Valves 44a, 46a respectively control fluid flow along first and second branches 44, 46 of return line 43. In one embodiment of the present invention, valves 44a, 46a take the form of pinch valves operable to open and close the fluid pathway through return line 43. Sections of tubing forming suction branches 44, 46 of return line 43 are respectively routed through the pinch valves that are controlled by the control unit of main unit 30. Furthermore, a one-way valve may be located within return line 43 to prevent backflow of fluid to surgical site 200.

Weight sensors 84, 86 may take the form of load cells that provide signals to main unit 30 indicative of the measured weight of fluid respectively collected in fluid collection containers 64, 66. The control unit of main unit 30 determines the volume of fluid collected in fluid collection containers 64, 66 from the measured weight.

Suction source 90 is fluidly connected with fluid collection containers 64, 66 (via suction line 33) and waste collection system 110 (via suction line 38). Waste collection system 110 is fluidly connected with fluid collection containers 64, 66 (via output line 53). Suction source 90 draws a vacuum in fluid collection containers 64, 66 (via suction line 33) to return fluid from surgical site 200 to fluid collection containers 64, 66 via return line 43. Suction source 90 also provides suction in suction line 38 and output line 53 to subsequently evacuate fluid collected in fluid collection container 64, 66 to waste collection system 110 via fluid output line 53. In the illustrated embodiment, suction source 90 takes the form of a vacuum pump.

Suction line 33 includes a first branch 34 and a second branch 36 for fluid communication with suction inputs (e.g., a suction tube) of fluid collection containers 64, 66, respectively. Branches 34 and 36 may be joined by a y-connector. Valves 34a, 36a respectively control suction along first and second branches 34, 36 of suction line 33. In one embodiment of the present invention, valves 34a, 36a may take the form of pinch valves operable to open and close the fluid pathway through suction line 33. Sections of tubing forming suction branches 34, 36 of suction line 33 are respectively routed through the pinch valves that are controlled by the control unit of main unit 30. Furthermore, a hydrophobic filter may be located within suction line 33 to prevent fluid from being sucked out of fluid collection containers 64, 66 through suction line 33. For example, hydrophobic filters may be located within branches 34 and 36 of suction line 33.

Output line 53 includes a first branch 54 and a second branch 56 for fluid communication with fluid outputs (e.g., a dip tube or bottom suction tube) of fluid collection containers 64, 66, respectively. Branches 54 and 56 may be joined by a y-connector. Valves 54a, 56a respectively control fluid flow along first and second branches 54, 56 of output line 53. In one embodiment of the present invention, valves 54a, 56a may take the form of pinch valves operable to open and close the fluid pathway through output line 53. Sections of tubing forming suction branches 54, 56 of suction line 53 are respectively routed through the pinch valves that are controlled by the control unit of main unit 30.

As indicated above, return line 43, suction line 33, and output line 53 take the form of fluid conduits, such as conventional medical grade flexible plastic tubing. In one embodiment of the present invention, the sections of tubing for branches 44, 46 (return line 43); branches 34, 36 (suction line 33); and branches 54, 56 (output line 53) may each include an integrated strain relief element that "snaps" into, or otherwise attaches to, a support structure (e.g., stand, mounting bracket, frame, etc.) of fluid management unit 20A. For example, the strain relief element may be mounted to a support stand 22, described below with reference to FIG. 5. It is also contemplated that the sections of tubing for branches 44, 46 (return line 43); branches 34, 36 (suction line 33); and branches 54, 56 (output line 53) that connect respectively with fluid input, suction input and fluid output of fluid collection containers 64, 66 have an accordion tubing component or section to allow for relaxed flexing and extension of the tubing. It should be appreciated that the strain relief element and accordion tubing section minimize forces applied to fluid collection containers 64, 66 as a result of "pushing and pulling" of the tubing. This minimizes disturbance to weight measurements made by weight sensors 84, 86, and thus provides for greater accuracy in fluid deficit monitoring.

FIG. 1 illustrates pass-through fluid volume measurement system 60 as a component of fluid management unit 20A. However, as will be described in detail below, the pass-through fluid volume measurement system of the present invention may alternatively be constructed as a stand-alone component that is separate from a fluid management unit. In this case, the strain relief element may attach to a support structure that independently supports pass-through fluid volume measurement system 60.

It is contemplated that waste collection system 110 may take a variety of different forms, including, but not limited to, a mobile fluid collection container or cart, a dedicated stand-alone fluid collection system with integrated suction, or a hospital's waste disposal system which may be accessible in the operating room.

In the illustrated embodiment, a combined tissue/air trap 132 (or individual tissue and air traps) is located within return line 43. A tissue trap (or other similar device) functions to collect tissue carried by fluid returning from surgical site 200 via return line 43 for subsequent analysis and/or to increase the accuracy of fluid deficit calculations. In the absence of a tissue trap, tissue returned from surgical site 200 can increase the weight of fluid collection canisters or interfere with fluid flow sensing measurements. Similarly, an air trap can increase the accuracy of fluid deficit calculations as air bubbles can interfere with fluid flow sensing measurements.

For enhanced safety, it is contemplated that measurement system 60 may also include one or more fluid level sensors for detecting the fluid level within fluid collection containers 64 and 66, and one or more leak sensors for detecting the presence of a leak in fluid collection containers 64, 66 or in a tubing connection associated therewith. A fluid level sensor determines, independently of the control unit of main unit 30, whether a fluid level has reached a predetermined fluid level within fluid collection containers 64, 66 and can close one or more of valves 44a, 46a, 34a, and 36a, if necessary. When a leak sensor detects the presence of a leak, the leak sensor transmits a signal to the control unit of main unit 30. In response to receipt of this signal, the control unit can take appropriate action, such as "closing" one or more of valves 44a, 46a, 34a, 36a and providing a visual and/or audible indicator to alert a user of a potential problem with measurement system 60.

The operation of FMS 10A will now be described in detail with reference to FIG. 1. At the beginning of a surgical procedure, fluid supply containers are mounted to main unit 30 and connected with fluid supply line 40 to supply fluid to surgical site 200. The volume of fluid supplied to surgical site 200 is monitored by main unit 30. In addition, two fluid collection containers 64, 66 are arranged to be independently weighed by respective weight sensors 84, 86. Respective strain relief elements are snapped into a support structure, and appropriate sections of tubing associated with branches 44, 46 (return line 43); branches 34, 36 (suction line 33); and branches 54, 56 (output line 53) are routed through corresponding valves 44a, 46a; 34a, 36a; and 54a, 56a, which take the form of pinch valves.

When a user initiates a procedure using main unit 30 that begins the flow of fluid to surgical site 200 via supply line 40, the control unit "zeroes" any previously stored weight values and begins recording the weight of each fluid collection container 64, 66 as indicated by respective weight sensors 84, 86. Then, valves 34a, 44a associated with the suction input and the fluid input of fluid collection container 64 are "opened" and valve 54a associated with the fluid output of fluid collection container 64 is "closed." Furthermore, valves 36a and 46a associated with the suction input and fluid input of fluid collection container 66 are "closed."

The control unit of main unit 30 monitors the volume of fluid supplied to the surgical site 200 and monitors the volume of fluid returned to fluid collection container 64 via signals received from weight sensor 84. When the fluid volume collected in fluid collection container 64 reaches a predetermined volume, the control unit "closes" valves 34a, 44a respectively associated with the suction input and the fluid input of fluid collection container 64, allows the weight sensor reading to stabilize, records the total weight of fluid collection container 64, and then "opens" valve 54a associated with the fluid output of fluid collection container 64 in order to empty fluid collection container 64 by evacuating the collected fluid to waste collection system 110. Simultaneously, the control unit "opens" valves 36*a* and 46*a* respectively associated with the suction input and the fluid input of fluid collection container 66, and "closes" valve 56*a* associated with the fluid output of fluid collection container 66 to begin filling fluid collection container 66 with the fluid returned from surgical site 200. In this manner, fluid collection from surgical site 200 and fluid deficit monitoring continues uninterrupted. The above-described "alternating" fill/empty process (i.e., alternating the filling and emptying of fluid collection containers 64 and 66), is repeated until the user ends the fluid collection procedure.

In accordance with the present invention, measurement system 60 is adapted to measure any amount of fluid returned from surgical site 200 during a medical procedure, without the burdensome and costly need to change fluid collection containers. Furthermore, the present invention allows fluid management unit 20A to continuously return fluid from surgical site 200, and thus allows uninterrupted determination of the fluid deficit which can be displayed to a user by visual and/or audible indicators (e.g., alarms) that may be appropriate based on the measured or calculated fluid deficit level.

Figure 2:
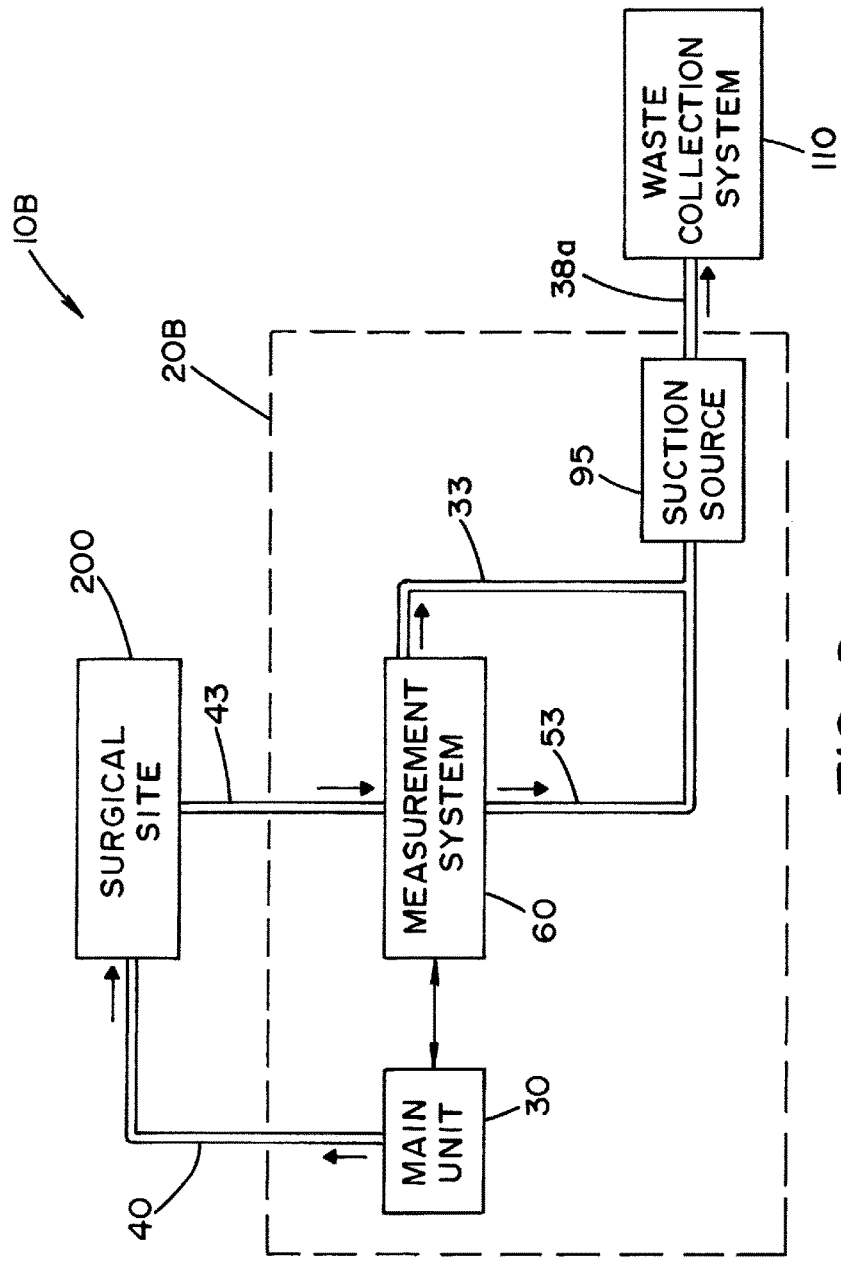
FIG. 2 is a schematic diagram illustrating an FMS according to a second embodiment of the present invention, wherein the FMS includes a fluid management unit having a pass-through fluid volume measurement system and an integrated suction source for return of fluid from the surgical site and subsequent evacuation of the fluid returned from the surgical site to a waste collection system.
Figure 3:
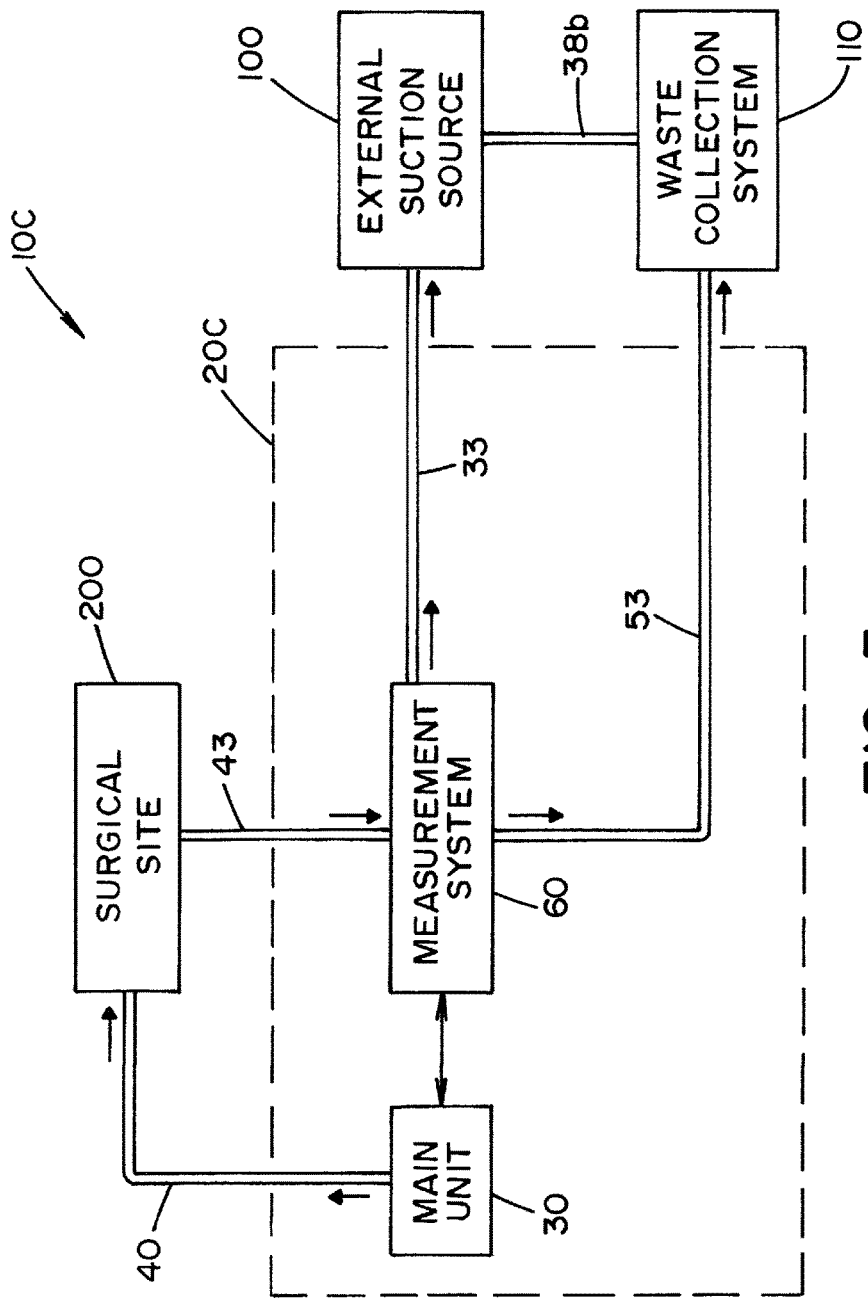
FIG. 3 is a schematic diagram illustrating an FMS according to a third embodiment of the present invention, wherein the FMS includes a fluid management unit with a pass-through fluid volume measurement system, and an external suction source for return of fluid from the surgical site and subsequent evacuation of the fluid returned from the surgical site to a waste collection system.
Figure 4:
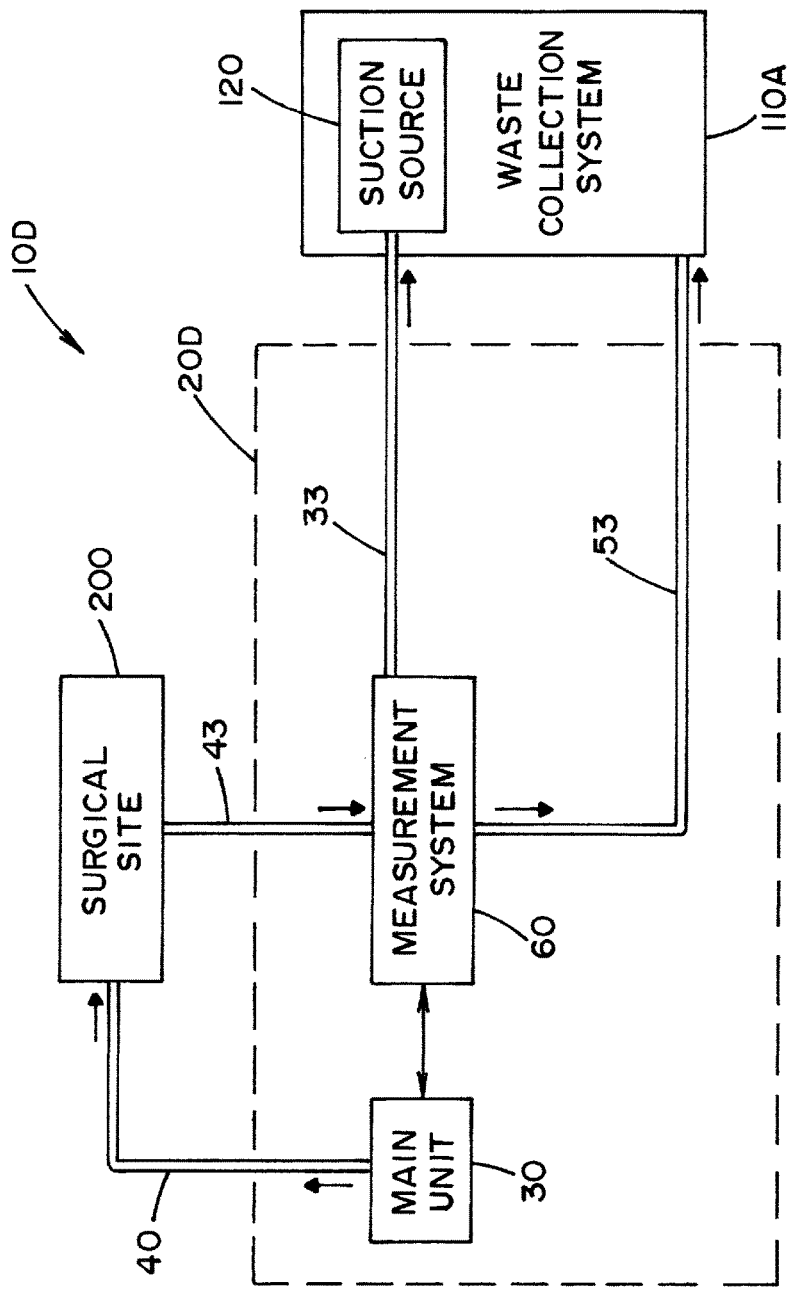
FIG. 4 is a schematic diagram illustrating an FMS according to a fourth embodiment of the present invention, wherein the FMS includes a fluid management unit with a pass-through fluid volume measurement system and a suction source of a waste collection system, wherein the suction source of the waste collection system provides suction for both return of fluid from the surgical site and subsequent evacuation of the fluid returned from the surgical site to the waste collection system.

FIGS. 2-4 illustrate fluid management systems according to alternative embodiments of the present invention. In these figures, components similar to those shown in FIG. 1 have been given the same reference numbers.

In the embodiment shown in FIG. 2, there is shown a FMS 10B having a fluid management unit 20B that includes an integrated suction source 95, which preferably takes the form of a pump. Suction source 95 provides suction in suction line 33 to return fluid from surgical site 200 to fluid collection containers 64, 66 and provides suction in output line 53 for evacuating fluid collected in fluid collection containers 64, 66 to waste collection system 110. It should be appreciated that suction source 95 may also be directly integrated into measurement system 60.

In the embodiment shown in FIG. 3, there is shown a FMS 10C having a fluid management unit 20C that does not include an integrated suction source and therefore fluid management unit 20C relies upon an external suction source 100 for suction. External suction source 100 may take the form of a conventional wall suction unit (e.g., vacuum pump) typically found in hospitals. External suction source 100 provides suction, via suction line 33, to return fluid from surgical site 200 to fluid collection containers 64, 66. External suction source 100 also provides suction via suction line 38*b* and output line 53 for evacuating fluid collected in fluid collection containers 64, 66 to waste collection system 110.

In the embodiment shown in FIG. 4, there is shown a FMS 10D having a fluid management unit 20D and a suction source 120 that is an integrated component of waste collection system 110. Suction source 120 may take the form of a conventional vacuum pump. Suction source 120 provides suction in fluid collection container 64, 66, via suction line 33, to draw fluid from surgical site 200 to fluid collection containers 64, 66. Suction source 120 also provides suction, via output line 53, for evacuating fluid collected in fluid collection containers 64, 66 to waste collection system 110.

It should be appreciated that the suction sources described herein (i.e., suctions source 90, 95, 100 and 120) may take a variety of forms including, but not limited to, a vacuum pump, a peristaltic pump, rotary vane pump, gerotor pump, piston pump, and the like.

Figure 6:
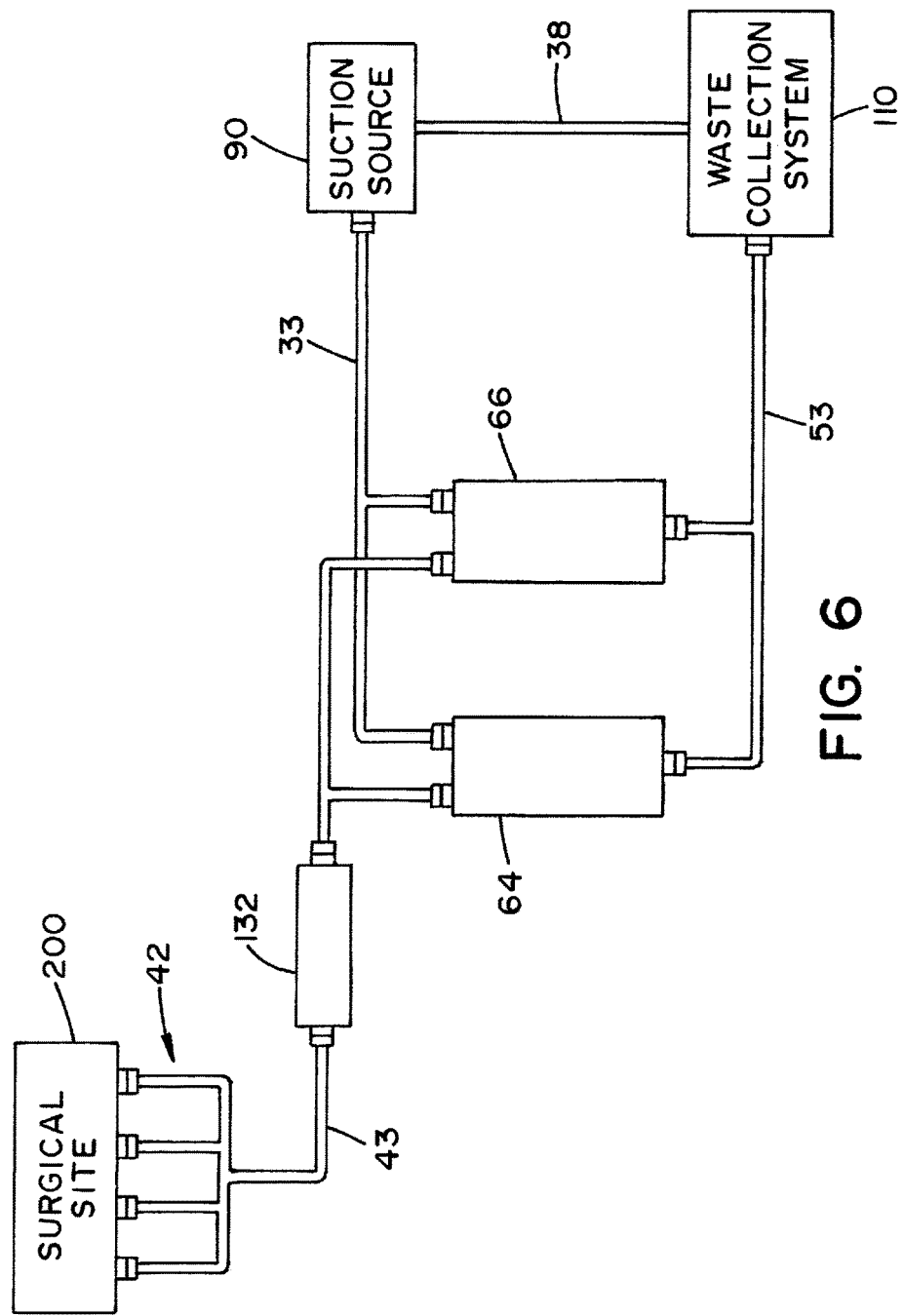
FIG. 6 illustrates a tubing set used in connection with the FMS embodiment shown in FIG. 1.

In accordance with an embodiment of the present invention, fluid collection containers 64, 66 and all tubing associated suction line 33, return line 43 and output line 53 are components of a single-use/disposable tubing set. For example, FIG. 6 illustrates a tubing set used in connection with FMS 10A (FIG. 1) that includes tubing for return line 43 (including a plurality of input branches 42), tubing for suction line 33, tubing for output line 53, and fluid collection containers 64 and 66. A tissue/air trap 132 may also be located in the tubing of return line 43. The tubing set may also include additional tubing for suction line 38 between suction source 90 and waste collection system 110.

Figure 7:
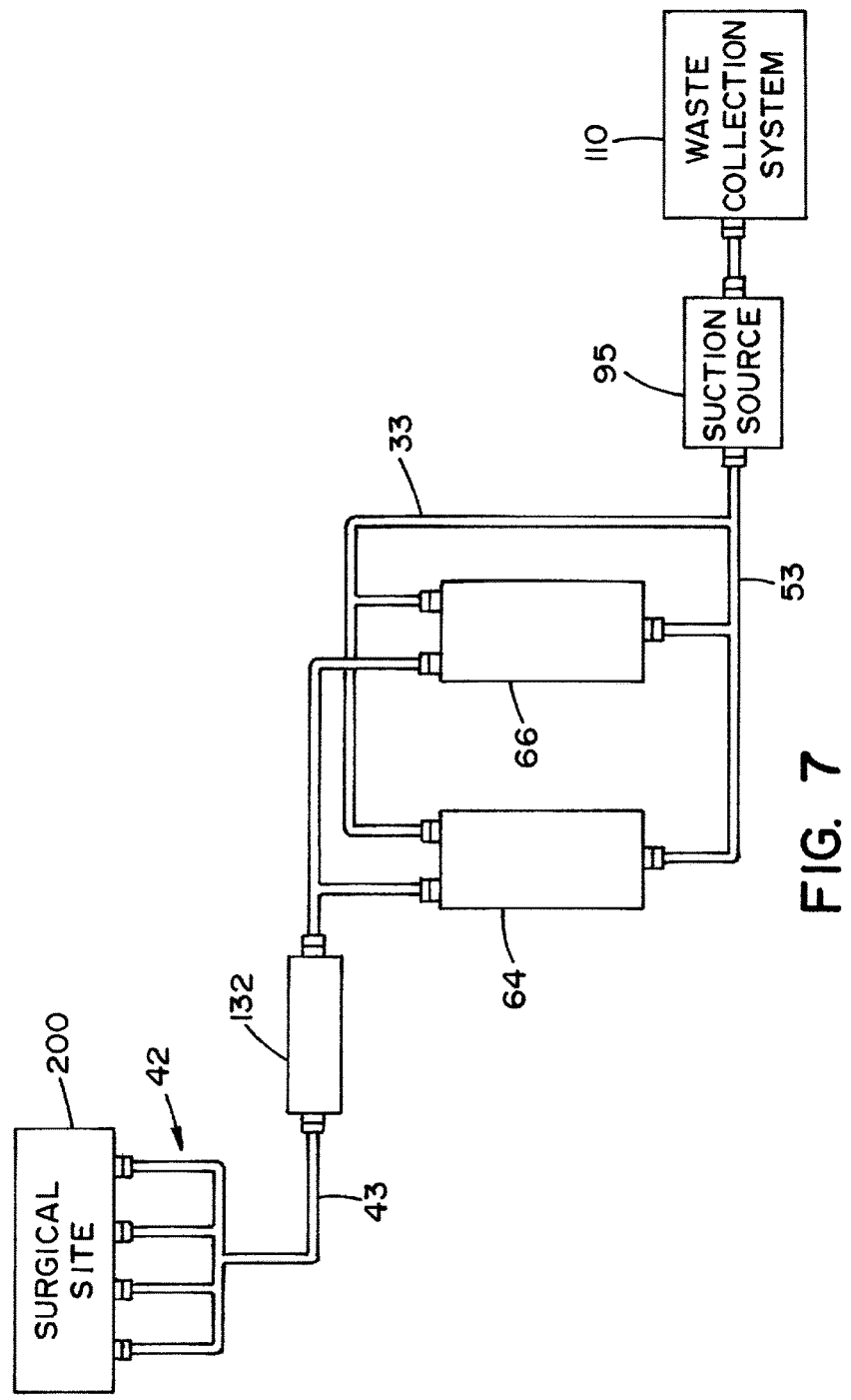
FIG. 7 illustrates a tubing set used in connection with the FMS embodiment shown in FIG. 2.

FIG. 7 illustrates a tubing set used in connection with FMS 10B (FIG. 2) that includes tubing for return line 43 (including a plurality of input branches 42), tubing for suction line 33, tubing for output line 53, and fluid collection containers 64 and 66. A tissue/air trap 132 may also be located in the tubing of return line 43. It should be appreciated that in this embodiment, the tubing for output line 53 is arranged through suction source 95.

Tubing sets similar to those illustrated in FIGS. 6 and 7 are used for the embodiments of FMS 10C and 10D respectively shown in FIGS. 3 and 4.

Figure 5:
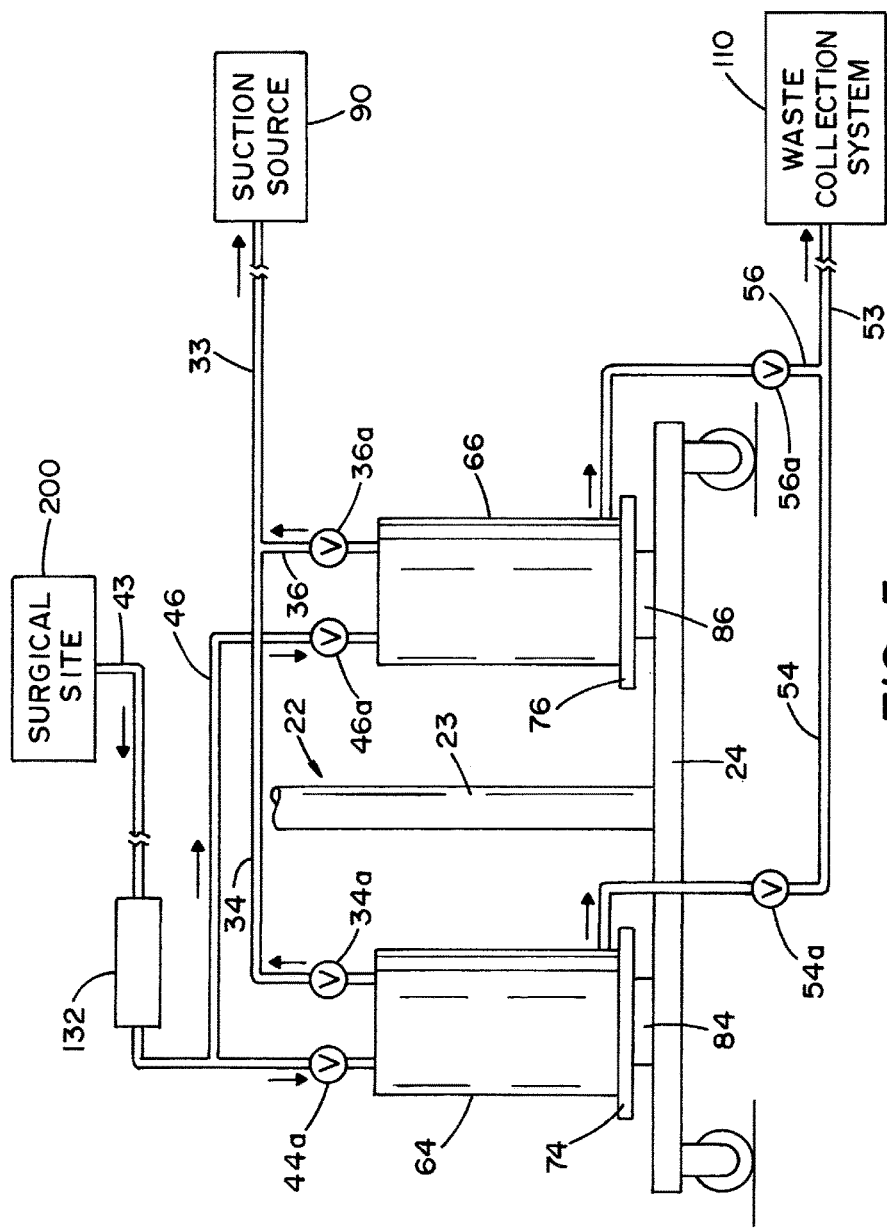
FIG. 5 is a schematic diagram illustrating a mechanical configuration of a pass-through fluid volume measurement system according an embodiment of the present invention.

Referring now to FIG. 5, there is shown a schematic diagram illustrating a mechanical embodiment of measurement system 60. Main unit 30, suction source 90 and measurement system 60 are mounted to portable support stand 22 having a pole 23 and a base 24 with wheels. In an alternative embodiment, main unit 30, suction source 90 and measurement system 60 may be mounted to a fixed support structure, such as a wall. Support members 74 and 76 (e.g., platform plates) respectively support fluid collection containers 64, 66. Weight sensor 84, 86 are mechanically connected with support members 74, 76. In the illustrated embodiment, fluid collection containers 64, 66 are each independently weighed by respective weight sensors 84, 86. Weight sensors 84, 86 provide signals to main unit 30 indicative of the respective measured weight of fluid collected in fluid collection containers 64, 66. Control unit of main unit 30 determines the volume of fluid collected in fluid collection containers 64, 66 from the measured weight.

Figure 8:
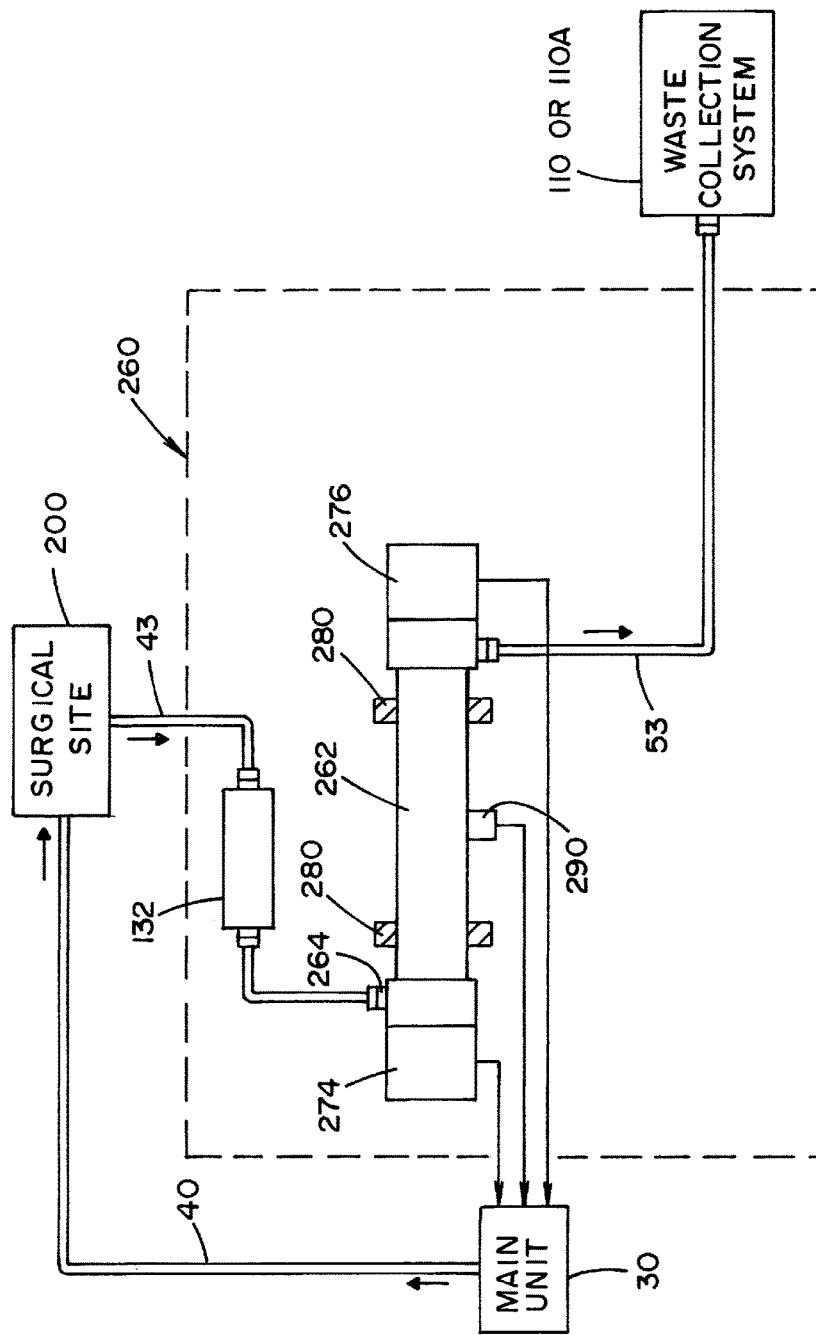
FIG. 8 is a schematic diagram of a pass-through fluid volume measurement system according to a first alternative embodiment, wherein suction is provided by a suction source external to the measurement system.

It is contemplated that the pass-through fluid volume measurement system of the present invention may take alternative forms. Referring now to FIG. 8, there is shown a pass-through fluid volume measurement system according to a first alternative embodiment. Measurement system 260 replaces the weight sensors and fluid collection containers of measurement system 60 with a fluid flow sensing device. In the illustrated embodiment, measurement system 260 is comprised of a fluid flow measurement tube 262 having an inlet port 264 at one end and an outlet port 266 at the opposite end, inlet and outlet ultrasonic sensors 274 and 276 (e.g., an ultrasonic transceiver, ultrasonic transmitter, or ultrasonic receiver) which are fixed or permanent components of measurement system 260, and a clamping mechanism 280 for temporarily mounting or attaching measurement tube 262 in a proper orientation between inlet and outlet ultrasonic sensors 274, 276. For example, clamping mechanism 280 may engage and capture measurement tube 262 with clamp or grip members (e.g., C-clamps). It is contemplated that clamping mechanism 280 may also include components that cause members supporting sensors 274, 276 to rotate, pivot, or move in order to properly position, orient or align sensors 274, 276 relative to measurement tube 262 to measure fluid volume in measurement tube 262. For example, installing a measurement tube 262 into engagement with clamping mechanism 280 may cause a spring-loaded sensor support member to press and hold sensors 274, 276 against the ends of measurement tube 262 in proper alignment. Sensors 274 and 276 are used to determine the flow rate of fluid passing through measurement tube 262. Sensors 274 and 276 provide signals, indicative of flow rate of fluid passing through measurement tube 262, to the control unit of main unit 30 (of a fluid management unit), which in turn determines the volume of fluid flowing through measurement tube 262. In the illustrated embodiment, measurement tube 262 is part of the single-use or disposable tubing set. Measurement tube 262 may also be a re-usable fluid tube that can be re-sterilized. Furthermore, sensors 274, 276 and clamping mechanism 280 may be permanently mounted to a support member (not shown) that supports components of measurement system 260. For example, such support member may take the form of a wall, cart, or stand.

It also contemplated that measurement system 260 may also include one or more temperature sensors 290 for sensing the temperature of the fluid in measurement tube 262. Temperature sensor 290 is properly oriented to measure the temperature of the fluid when measurement tube 262 is received into clamping mechanism 280. Temperature sensor 290 provides fluid temperature information to the control unit of main unit 30, which uses the temperature information to more accurately determine the fluid flow rate through measurement tube 262.

Furthermore, measurement system 260 may also include an accumulator in addition to combined tissue/air trap 132. The accumulator conditions the fluid prior to entering measurement tube 262 by absorbing surges or pulsations in the fluid flow.

Ultrasonic flowmeters use sound waves to determine the velocity of a fluid flowing in a pipe or tube. At "no flow" conditions, the frequencies of an ultrasonic wave transmitted into the tube and its reflections from the fluid are the same. Under flowing conditions, the frequency of the reflected wave is different due to the Doppler effect. When the fluid moves faster, the frequency shift increases linearly. Signals from the transmitted wave and its reflections are processed to determine the flow rate. A "transit time" ultrasonic flowmeter sends and receives ultrasonic waves between transducers in both the upstream and downstream directions in the tube. At "no flow" conditions, it takes the same time to travel upstream and downstream between the two transducers. Under flowing conditions, the upstream wave will travel slower and take more time than the (faster) downstream wave. When the fluid moves faster, the difference between the upstream and downstream times increases. Upstream and downstream times are processed to determine the flow rate.

For the embodiment of measurement system 260 shown in FIG. 8, an external suction source 100 or a suction source 120 internal to a waste collection system 110A provides the suction to draw fluid from surgical site 200 through return line 43, measurement tube 262, and output line 53 to the waste collection system.

Figure 9:
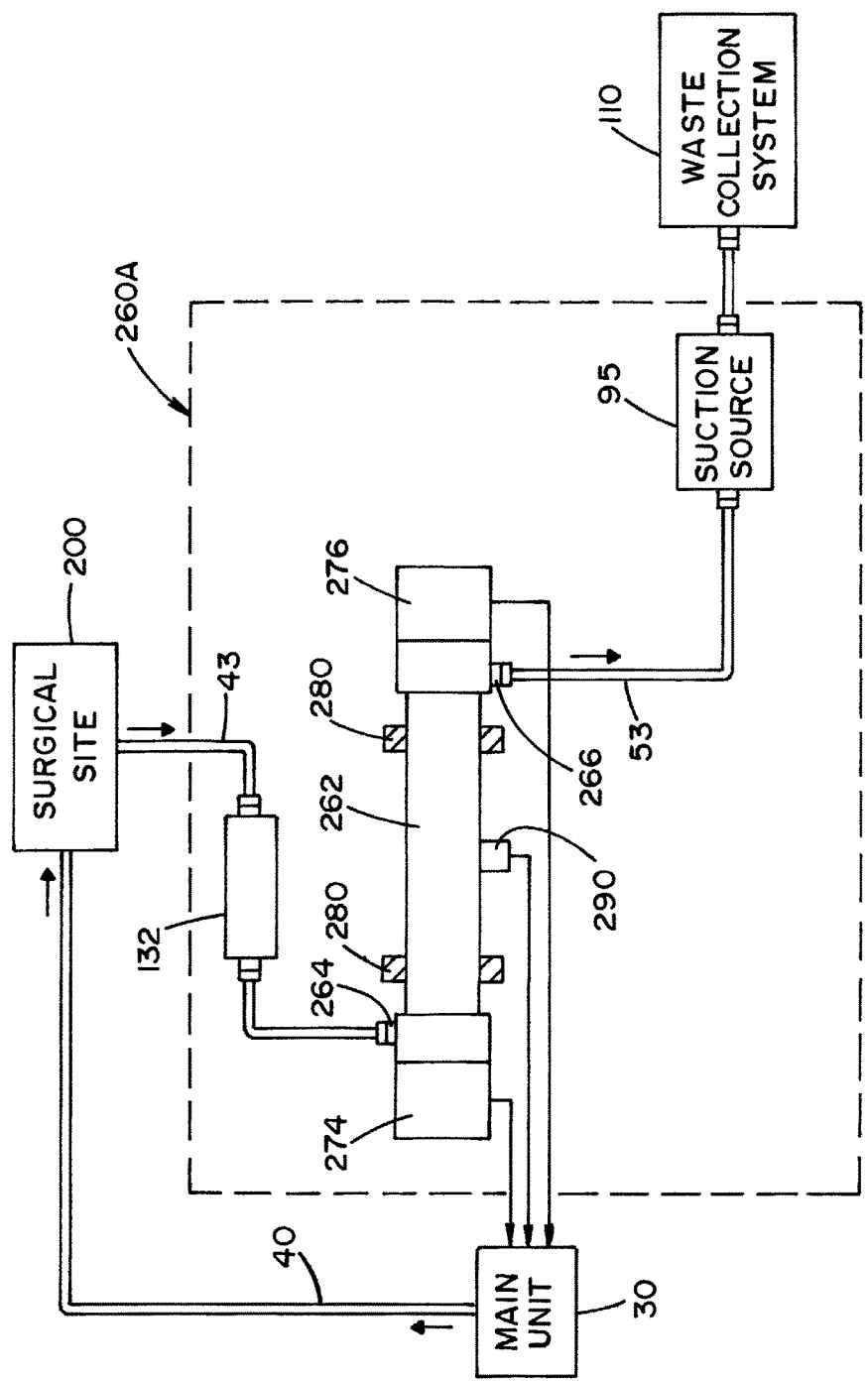
FIG. 9 is a schematic diagram of the pass-through fluid volume measurement system according to a second alternative embodiment, wherein suction is provided by a suction source integrated in the pass-through fluid volume measurement system.

In FIG. 9 a pass-through fluid volume measurement system 260A includes an integrated suction source 95 to provide suction for drawing fluid from surgical site 200 through return line 43, measurement tube 262, and output line 53 to waste collection system 110. Suction source 95 takes the form of a pump, wherein suction line 53 extends through suction source 95.

Figure 10:
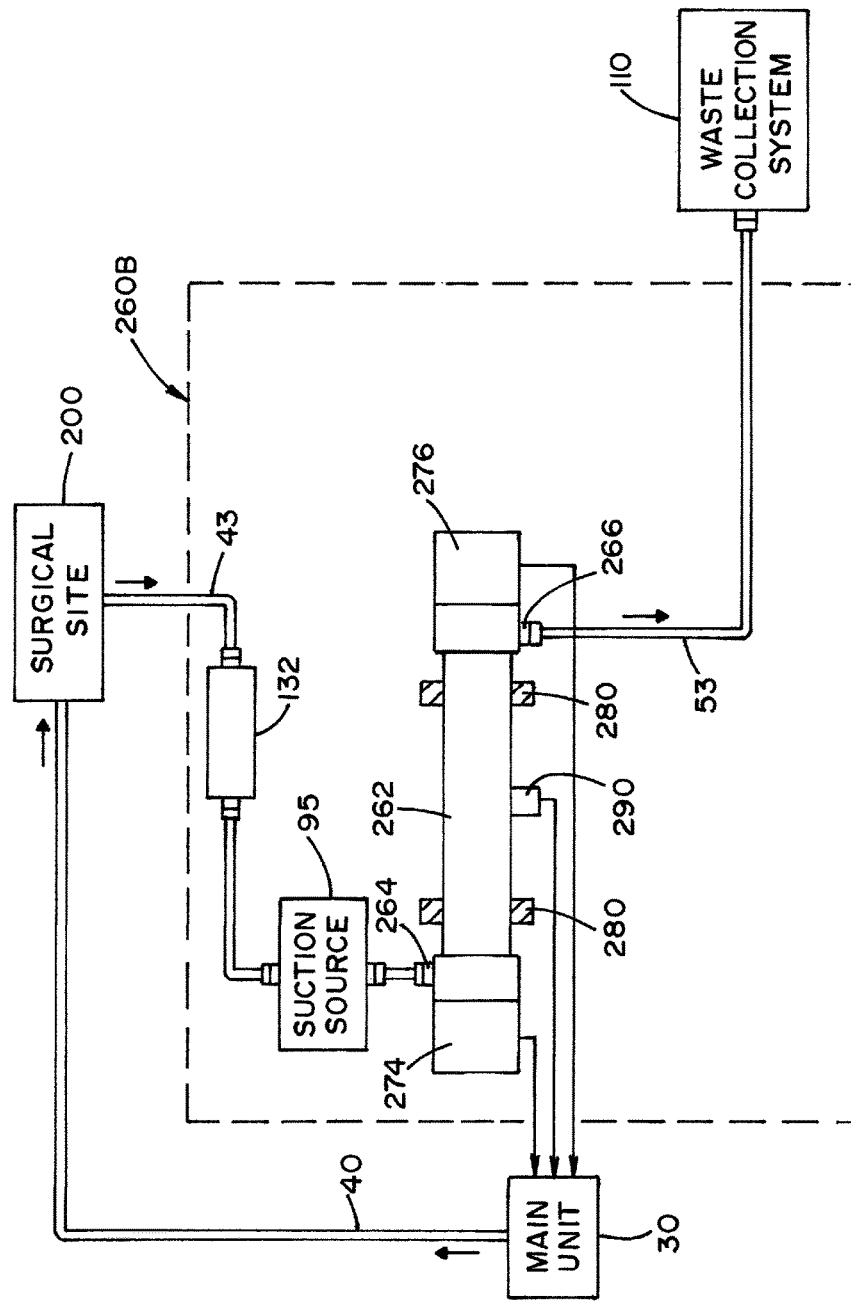
FIG. 10 is a schematic diagram of the pass-through fluid volume measurement system according to a third alternative embodiment, wherein suction is provided by a suction source integrated in the pass-through fluid volume measurement system.

In FIG. 10 a pass-through fluid volume measurement system 260B also includes an integrated suction source 95 to provide suction for drawing fluid from surgical site 200 through return line 43, measurement tube 262, and output line 53 to waste collection system 110. Suction source takes the form of a pump, wherein return line 43 extends through suction source 95.

It is contemplated in another alternative embodiment that the two ultrasonic sensors 274, 276 may be arranged in positions relative to measurement tube 262 that differ from the positions as depicted in the illustrated figures. For example, ultrasonic sensors 274, 276 may be located at the top and bottom portions of measurement tube 262. Furthermore, it is also contemplated that the measurement system may be configured with only a single ultrasonic sensor (e.g., an ultrasonic transceiver) for determining the volume of fluid flowing through measurement tube 262. For example, FIG. 10A illustrates a measurement system 260C that is a modified version of measurement system 260B (FIG. 10), wherein a single ultrasonic sensor 278 is substituted for sensors 274, 276. Single ultrasonic sensor 278 may take the form of a sensor or transducer that measures the deviation of the angle of reflected ultrasound to determine fluid flow rate.

Figure 11:
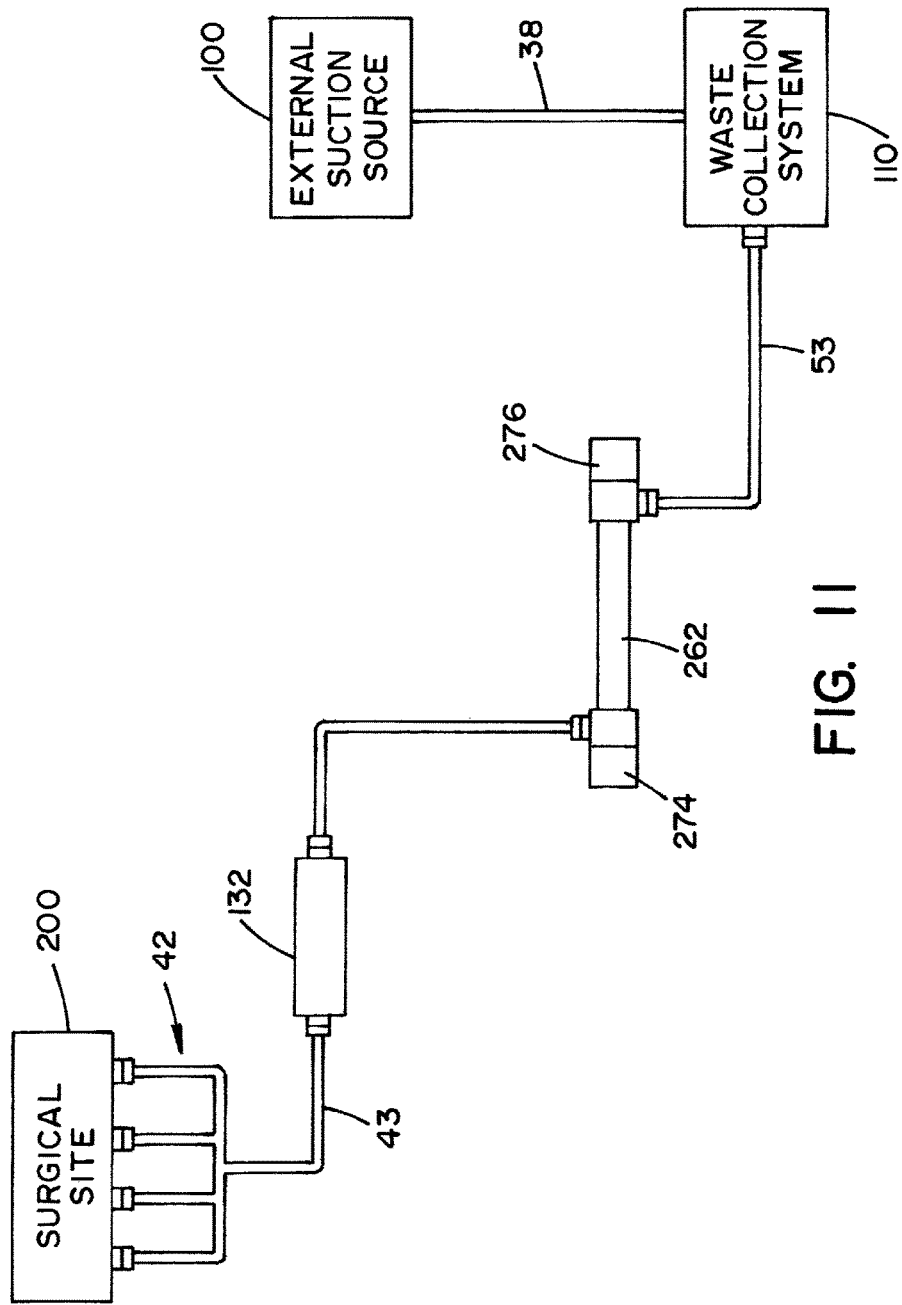
FIG. 11 illustrates a tubing set used in connection with the pass-through fluid volume measurement system shown in FIG. 8.

In accordance with an embodiment of the present invention, measurement tube 262, return line 43 and output line 53 are components of a single-use/disposable tubing set. For example, FIG. 11 illustrates a tubing set used in connection with measurement system 260 (FIG. 8) that includes tubing for return line 43 (including a plurality of input branches 42) and tubing for output line 53. A tissue/air trap 132 may also be located in the tubing of return line 43. The tubing set may also include additional tubing for suction line 38 between external suction source 100 and waste collection system 110. It should be appreciated that in the embodiment illustrated in FIG. 11, that waste collection system 110 and external suction source 100 can be replaced with waste collection system 110A having an internal suction source 120. In this embodiment, tubing for suction line 38 is omitted.

Figure 12:
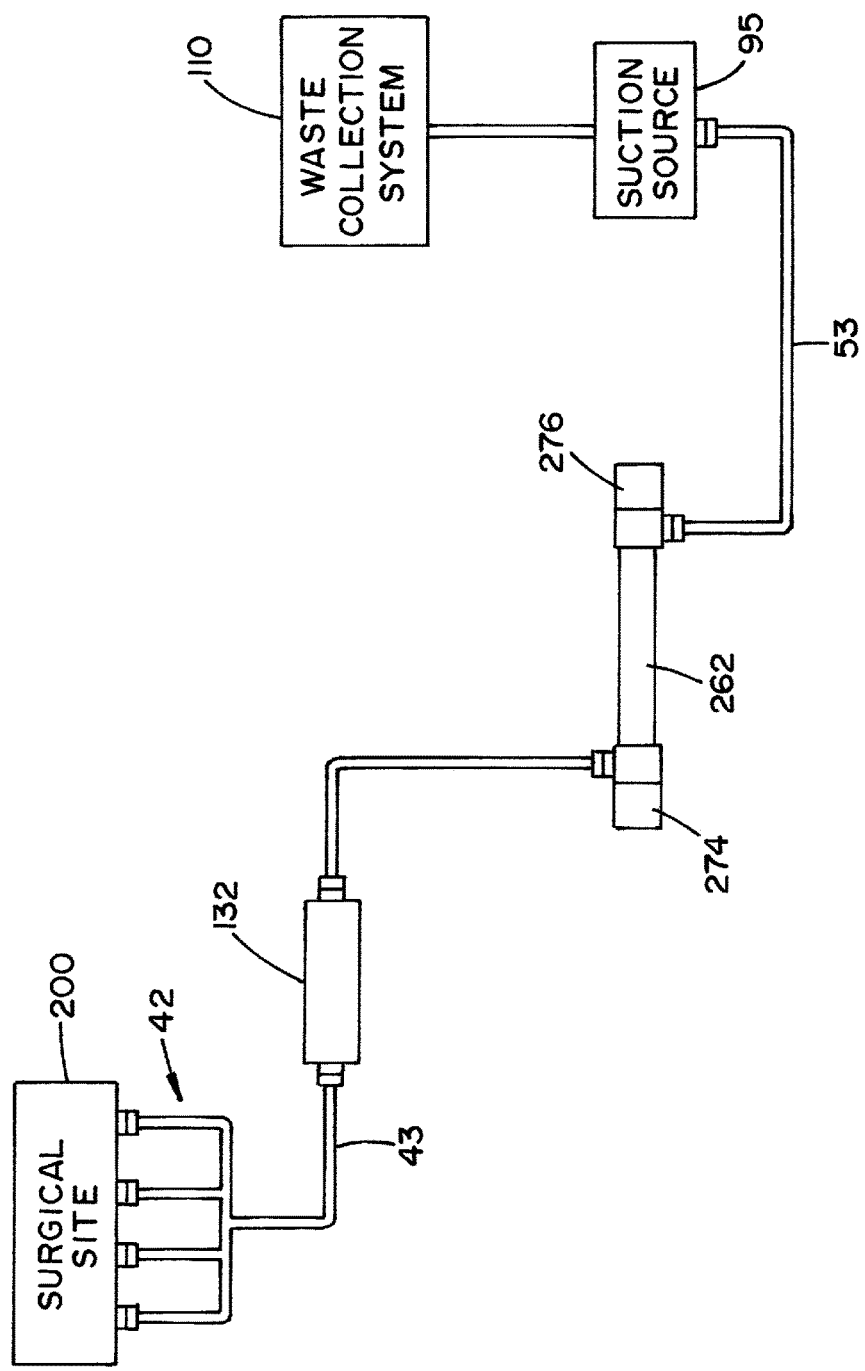
FIG. 12 illustrates a tubing set used in connection with the pass-through fluid volume measurement system shown in FIG. 9.

FIG. 12 illustrates a tubing set used in connection with measurement system 260A (FIG. 9) that includes tubing for return line 43 (including a plurality of input branches 42) and tubing for output line 53. A tissue/air trap 132 may also be located in the tubing of return line 43. It should be appreciated that in this embodiment, the tubing for output line 53 is arranged through suction source 95 that takes the form of a pump.

Figure 13:
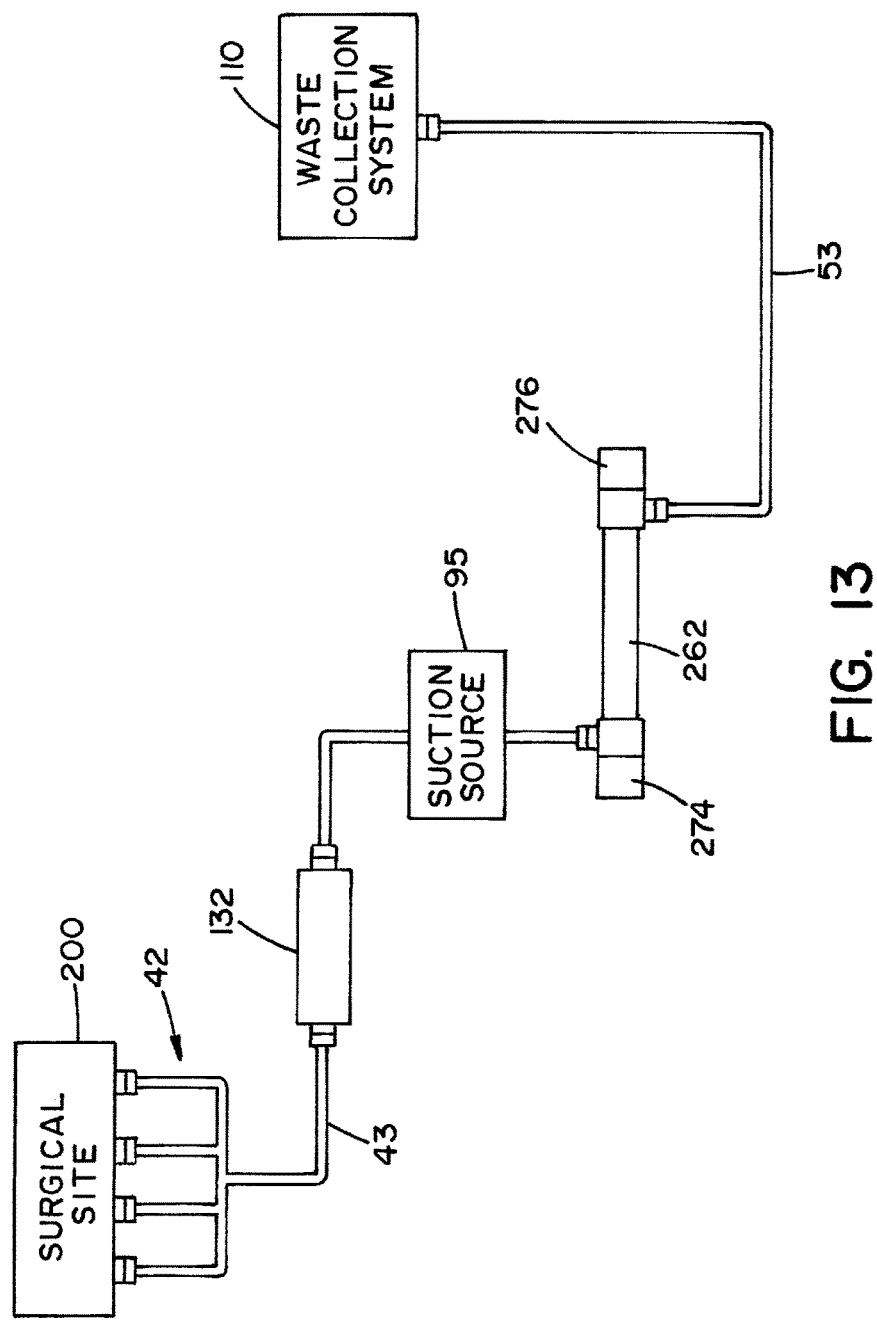
FIG. 13 illustrates a tubing set used in connection with the pass-through fluid volume measurement system shown in FIG. 10.

FIG. 13 illustrates a tubing set used in connection with measurement system 260B (FIG. 10) that includes tubing for return line 43 (including a plurality of input branches 42) and tubing for output line 53. A tissue/air trap 132 may also be located in the tubing of return line 43. It should be appreciated that in this embodiment, the tubing for return line 43 is arranged through suction source 95.

It should be appreciated that according to an alternative embodiment of the present invention, measurement systems 60 and 260 (including alternative embodiments 260A and 260B) may be configured as stand-alone devices that are physically separated from the fluid management unit. In this alternative embodiment, measurement systems 60, 260 may include their own control unit (independent of the control unit of main unit 30) having a microprocessor/microcontroller, display unit, and input unit. According to this embodiment, the control unit of the measurement system may perform some of the functions (described above) that are carried out by the control unit of main unit 30. Furthermore, measurement systems 60, 260 may also include a wireless or wired communications interface for communicating with main unit 30 of the fluid management unit via a wireless or wired communications medium. As a stand-alone device, measurement systems 60, 260 may be mounted to a portable support structure (e.g., a cart or mobile stand) or fixed support structure (e.g., a wall). Furthermore, the strain relief element discussed above may attach to the support structure that independently supports stand-alone measurement systems 60, 260.

It is contemplated that a variety of modifications and alterations may be made to the illustrated embodiments of the present invention without departing from the spirit and scope of the present invention. For example, the number of fluid collection containers and weight sensors may be greater than the number of fluid collection containers shown in the embodiments described above. In one alternative embodiment, a single weight sensor may be used to sense the weight of multiple fluid collection containers. Moreover, it is contemplated that other suitable means may be substituted for the weight sensors to detect the volume of fluid in the fluid collection containers (e.g., means for counting pump rotations or height of water column as determined through optical sensing). In addition, other types of tube constricting devices may be substituted for the above-described valves, including manually-controllable devices.

It is further contemplated that the accuracy of fluid deficit calculations may be improved by using an opacity meter to provide information indicative of the composition of the fluid returned from the surgical site. In this regard, the opacity meter provides a signal to the control unit of main unit 30 that can be used to ascertain or estimate the percentage of blood that comprises the fluid returned from the surgical site. For example, an opacity meter could be used to sense the opacity of the fluid flowing through return line 43, collected in fluid collection containers 64, 66, flowing through measurement tube 262, or flowing through output line 53.

Other modifications and alterations will occur to others upon their reading and understanding of the specification. It is intended that all such modifications and alterations be included insofar as they come within the scope of the invention as claimed or the equivalents thereof.

Having described the invention, the following is claimed:

1. A fluid management system comprising:
   at least one fluid supply container for storing a fluid to be delivered to a surgical site;
   a fluid supply line for delivering the fluid from the at least one fluid supply container to the surgical site; and
   a pass-through fluid volume measurement system for determining the volume of fluid returned from the surgical site, said pass-through fluid volume measurement system comprising:
      a plurality of fluid collection containers, wherein each fluid collection container has (i) a suction input in fluid communication with a suction line, for drawing a vacuum in the fluid collection container, (ii) a fluid input in fluid communication with a fluid return line for receiving fluid returning from the surgical site, and (iii) a fluid output in fluid communication with a fluid output line for evacuating the fluid collected in the fluid collection container to a waste collection system;
      one or more sensors for providing signals indicative of an amount of fluid in the fluid collection containers; and
      a plurality of valves moveable between open and closed positions to control the flow of fluid through the suction line, the fluid return line and the fluid output line;
      one or more suction sources for providing suction in the suction line to draw a vacuum in the fluid collection containers to thereby draw fluid from the surgical site into the fluid collection containers, and for providing suction in the fluid output line to draw fluid collected in the fluid collection containers into the waste collection system; and
      a control unit for receiving the signals from the one or more sensors to monitor a volume of fluid returned from the surgical site to the fluid collection containers, and moving the plurality of valves between the open and the closed positions to alternately fill one of the fluid collection containers while emptying another of the fluid collection containers.

2. The fluid management system according to claim 1, wherein said one or more sensors are optical sensors, weight sensors, or load cells.

3. The fluid management system according to claim 1, wherein said control unit continuously monitors the volume of fluid delivered to and returned from the surgical site to continuously determine a fluid deficit between the amount of fluid delivered to the surgical site and the amount of fluid returned from the surgical site to the fluid collection containers.

4. The fluid management system of claim 1, wherein the waste collection system is one of the following: a mobile fluid collection container or cart, dedicated stand-alone fluid collection system with integrated suction, or a hospital waste disposal system.

5. The fluid management system of claim 1, wherein the pass-through fluid volume measurement system further comprises:
   fluid level sensors for detecting whether a fluid level of one of the fluid collection containers has reached a predetermined fluid level.

6. The fluid management system of claim 1, wherein the system includes a tubing set comprised of:
   the plurality of fluid collection containers;
   a first tubing portion providing the suction line connected to the suction input of each of the fluid collection containers;
   a second tubing portion providing the fluid input line connected to the fluid input of each of the fluid collection containers; and
   a third tubing portion providing the fluid output line connected to the fluid output of each of the fluid collection containers.

7. The fluid management system of claim 6, wherein the tubing set further comprises a tissue collection trap.

8. The fluid management system of claim 7, wherein the tissue collection trap is located in the second tubing portion.

9. The fluid management system of claim 6, wherein each of the first, second and third tubing portions has an associated strain relief element.

10. The fluid management system of claim 6, wherein the tubing set further comprises a hydrophobic filter in the first tubing portion to prevent fluid from flowing toward the suction source in the suction line.

11. The fluid management system of claim 6, wherein the tubing set further comprises a check valve in the second tubing portion to prevent fluid from back flowing to the surgical site.

12. The fluid management system according to claim 1, wherein said suction source is a component of the pass-through volume measurement system.

13. The fluid management system according to claim 1, wherein said fluid collection containers are re-usable.

14. The fluid management system according to claim 1, wherein said suction source is located external to the pass-through volume measurement system.

15. The fluid management system according to claim 14, wherein said suction source is a component of the waste collection system.

16. The fluid management system according to claim 1, wherein said suction source is one of the following: a vacuum pump, a peristaltic pump, rotary vane pump, gerotor pump, or a piston pump.

17. The fluid management system according to claim 1, wherein the plurality of valves are pinch valves.

18. The fluid management system according to claim 1, wherein said control unit is a component of the pass-through volume measurement system.

19. The fluid management system of claim 1, wherein the pass-through fluid volume measurement system further comprises:
- at least one leak sensor for detecting the presence of a fluid leak in at least one of the following: the fluid collection containers, the fluid return line, and the fluid output line.

20. The fluid management system of claim 1, wherein the at least one fluid supply container and the pump are components of a fluid management unit, said pass-through volume measurement system including a communications interface for communicating with a control unit of the fluid management unit via wired or wireless communications.

* * * * *